United States Patent [19]

Asaka et al.

[11] Patent Number: 4,886,748

[45] Date of Patent: Dec. 12, 1989

[54] DNA ENCODING FLAGELLIN AND VECTOR HAVING THE SAME

[75] Inventors: Junichiro Asaka, Sakai; Tamio Fujiwara, Amagasaki; Takashi Fujiwara, Nara; Goro Kuwajima, Nishinomiya; Eiji Kondo, Ikeda; Masaru Shin, Kobe, all of Japan

[73] Assignee: Shionogi & Co., Ltd., Osaka, Japan

[21] Appl. No.: 24,992

[22] Filed: Mar. 11, 1987

[30] Foreign Application Priority Data

Mar. 11, 1986 [JP] Japan .................................. 61-54400
Sep. 19, 1986 [JP] Japan ................................ 61-223484

[51] Int. Cl.$^4$ ...................... C12P 21/00; C12P 21/02; C12N 5/00; C12N 15/00
[52] U.S. Cl. ............................... 435/69.7; 435/172.3; 435/252.33; 435/320; 536/27; 935/11; 935/29; 935/39; 935/44; 935/56; 935/60; 935/73
[58] Field of Search ..................... 435/68, 70, 91, 253, 435/172.3, 320; 935/11, 29, 39, 44, 56, 60, 73; 536/27

[56] References Cited

PUBLICATIONS

Szekely et al., *J. Bact.*, vol. 155, pp. 74–81, 1983, "DNA Sequence Adjacent to Flagellar Genes and Evolution of Flagellar Phase Variation".
Kondoh et al., *J. Bact*, vol. 130, pp. 736–745, 1977, "Isolation and Characterization of Nondefective Transducing Lamda Bacteriophages Carrying Fla genes of Eschericha coli K-12".
Joys et al., *J. Bio. Chem.*, vol. 260, pp. 15758–1576, 1985, "The Covalent Structure of the Phase-1 Flagellar Filament Protein of Salmonella Typhimurium and Its Comparison with Other Flagellins".
Wei et al., 1985, *J. Mol. Biol.*, vol. 186, pp. 791–803, "Covalent Structure of Three Phase-1 Flagellar Filament Proteins of Salmonella".
Gill et al., *J. Biol. Chem.*, vol. 258, pp. 7395–7401, 1983, "The Nucleotide Sequence of the $M_1=28,500$ Flagellin Gene of Caulobacter Crescentus".

*Primary Examiner*—Robin Teskin
*Attorney, Agent, or Firm*—Birch, Stewart, Kolasch & Birch

[57] ABSTRACT

The whole DNA sequence coding for flagellin of *E. coli* (hag gene) cloned in phage λ was determined. The hag gene is introduced into pBR322 and the region of the hag gene concerning the antigencity of flagella is lacked, into which linkers are inserted. Where the vector in which foreign DNA is inserted in the linker is introduced in *E. coli* forming no flagella, the *E. coli* can form flagella and possesses motility. The flagella comprises flagellin fused with foreign peptide encoded by the foreign DNA. Namely, the foreign peptide is excreted outside of bacteria. This system can be utilized in determination of epitope and preparation of antigen as well as excretion of peptide.

31 Claims, 38 Drawing Sheets

Fig.1-1

```
  10                20                30
ATGGCACAAGTCATTAATACCAACAGCCTC
MetAlaGlnValIleAsnThrAsnSerLeu
  40                50                60
TCGCTGATCACTCAAAATAATATCAACAAG
SerLeuIleThrGlnAsnAsnIleAsnLys
  70                80                90
AACCAGTCTGCGCTGTCGAGTTCTATCGAG
AsnGlnSerAlaLeuSerSerSerIleGlu
 100               110               120
CGTCTGTCTTCTGGCTTGCGTATTAACAGC
ArgLeuSerSerGlyLeuArgIleAsnSer
 130               140               150
GCGAAGGATGACGGCAGCGGGTCAGGCGATT
AlaLysAspAspAlaSerGlyGlnAlaIle
 160               170               180
GCTAACCGTTTCACCTCTAACATTAAAGGC
AlaAsnArgPheThrSerAsnIleLysGly
 190               200               210
CTGACTCAGGCGGCCCCGTAACGCCAACGAC
LeuThrGlnAlaAlaArgAsnAlaAsnAsp
 220               230               240
GGTATCTCCGTTGCGCAGACCACCGAAGGC
GlyIleSerValAlaGlnThrThrGluGly
 250               260               270
GCGCTGTCCGAAATCAACAACAACTTACAG
AlaLeuSerGluIleAsnAsnAsnLeuGln 280               290               300
CGTGTGCGTGAACTGACGGTACAGGCCACT
ArgValArgGluLeuThrValGlnAlaThr
 310               320               330
ACCGGTACTAACTCTGAGTCTGATCTGTCT
ThrGlyThrAsnSerGluSerAspLeuSer
 340               350               360
TCTATCCAGGACGAAATTAAATCCCGTCTG
SerIleGlnAspGluIleLysSerArgLeu
 370               380               390
GATGAAATTGACCGCGTATCTGGTCAGACC
AspGluIleAspArgValSerGlyGlnThr
 400               410               420
CAGTTCAACGGCGTGAACGTGCTGGCAAAA
GlnPheAsnGlyValAsnValLeuAlaLys
 430               440               450
AATGGCTCCATGAAAATCCAGGTTGGCGCA
AsnGlySerMetLysIleGlnValGlyAla
 460               470               480
AATGATAACCAGACTATCACTATCGATCTG
AsnAspAsnGlnThrIleThrIleAspLeu
 490               500               510
AAGCAGATTGATGCTAAAACTCTTGGCCTT
LysGlnIleAspAlaLysThrLeuGlyLeu
 520               530               540
GATGGTTTTAGCGTTAAAAATAACGATACA
AspGlyPheSerValLysAsnAsnAspThr
```

Fig.1-2

```
 550                          570                          820                          840
GTTACCACTAGTGCTCCAGTAACTGCTTT                        GCAAATACTACTAAAGCTACAAACTACT
ValThrThrSerAlaProValThrAlaPhe                       AlaAsnThrThrLysAlaThrThrIleThr 580                          600                          850                          870
GGTGCTACCACCACAAACAATATTAAACTT                       TCAGGCGGTACACCTGTTCAGATTGATAAT
GlyAlaThrThrThrAsnAsnIleLysLeu                       SerGlyGlyThrProValGlnIleAspAsn 610                          630                          880                          900
ACTGGAATTACCCTTTCTACGGAAGCAGCC                       ACTGCAGGTTCCCGCAACTGCCAACCTTGGT
ThrGlyIleThrLeuSerThrGluAlaAla                       ThrAlaGlySerAlaThrAlaAsnLeuGly 640                          660                          910                          930
ACTGACTGGCGCGGAACTAACCCCAGCTTCA                      GCTGTTAGCTTAGTAAAACTGCAGGATTCC
ThrAspThrGlyGlyThrAsnProAlaSer                       AlaValSerLeuValLysLeuGlnAspSer 670                          690                          940                          960
ATTGAGGGTGTTTATACTGATAATGGTAAT                       AAGGGTAATGATACCGATACATATGCGCTT
IleGluGlyValTyrThrAspAsnGlyAsn                       LysGlyAsnAspThrAspThrTyrAlaLeu 700                          720                          970                          990
GATTACTATGCGAAAATCACCCGGTGGTGAT                      AAAGATACAAATGGCAATCTTTACGGCTGCG
AspTyrTyrAlaLysIleThrGlyGlyAsp                       LysAspThrAsnGlyAsnLeuTyrAlaAla 730                          750                         1000                         1020
AACGATGGAAGTATTACGCAGTAACAGTT                        GATGTGAATGAAAACTACTGGTGCTGTTTCT
AsnAspGlySerIleTyrTyrAlaValThrVal                    AspValAsnGluThrThrGlyAlaValSer 760                          780                         1030                         1050
GCTAATGATGGTACAGTGACAATGGCGACT                       GTTAAAACTATTACCTATACTGACTCTTCC
AlaAsnAspGlyThrValThrMetAlaThr                       ValLysThrIleThrTyrThrAspSerSer 790                          810                         1060                         1080
GGAGCAACGGCAAATGCAACCTGTAACTGAT                      GGTGCCGCCAGTTCTCCAACCGCCGGTCAAA
GlyAlaThrAlaAsnAlaThrValThrAsp                       GlyAlaAlaSerSerProThrAlaValLys
```

Fig.1-3

```
                    1090            1100            1110
CTGGGCGGAGATGATGGCAAAAACAGAAGTG
LeuGlyGlyAspAspGlyLysThrGluVal
         1120            1130            1140
GTCGATATTGATGGTAAAACATACGATTCT
ValAspIleAspGlyLysThrTyrAspSer
         1150            1160            1170
GCCGATTTAAATGGCGGTAATCTGCAAACA
AlaAspLeuAsnGlyGlyAsnLeuGlnThr
         1180            1190            1200
GGTTTGACTGCTGGTGGTGAGGCTCTGACT
GlyLeuThrAlaGlyGlyGluAlaLeuThr
         1210            1220            1230
GCTGTTGCAAATGGTAAAACCACGGATCCG
AlaValAlaAsnGlyLysThrThrAspPro
         1240            1250            1260
CTGAAAGCGCTGGACGATGCTATCGCATCT
LeuLysAlaLeuAspAspAlaIleAlaSer
         1270            1280            1290
GTAGACAAATTCCGTTCTTCCCTCGGTGCG
ValAspLysPheArgSerSerLeuGlyAla
         1300            1310            1320
GTGCAAAACCGTCTGGATTCCGCGGTTACC
ValGlnAsnArgLeuAspSerAlaValThr
         1330            1340            1350
AACCTGAACAACACCACTACCAACCTGTCT
AsnLeuAsnAsnThrThrThrAsnLeuSer
```

```
         1360            1370            1380
GAAGCGCAGTCCCGTATTCAGGACGCCGAC
GluAlaGlnSerArgIleGlnAspAlaAsp
         1390            1400            1410
TATGCGACCGAAGTGTCCAATATGTCGAAA
TyrAlaThrGluValSerAsnMetSerLys
         1420            1430            1440
GCCGAGATCATCCAGCAGGCCGGTAACTCC
AlaGluIleIleGlnGlnAlaGlyAsnSer
         1450            1460            1470
GTGTTGGCAAAAGCTAACCAGGTACCGCAG
ValLeuAlaLysAlaAsnGlnValProGln
         1480            1490
CAGGTTCTGTCTCTGCTGCAGGGT
GlnValLeuSerLeuLeuGlnGly
```

▽ EcoRI

▼ SalI

A : 21.3 Kb          C : 5.82 Kb

F : 3.54 Kb         b : 15.3 Kb

▽ EcoRI

▼ SalI

☐ 3.7 Kb DNA

▨ 7.5 Kb DNA

Fig. 4
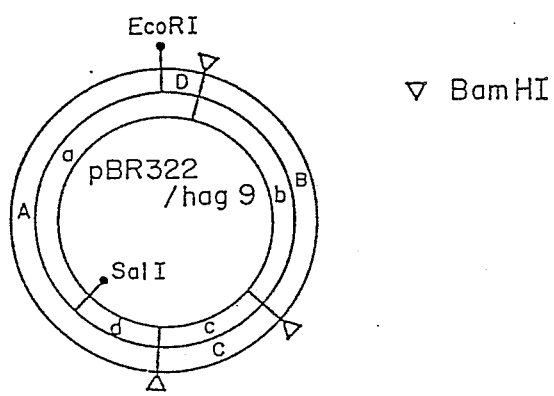
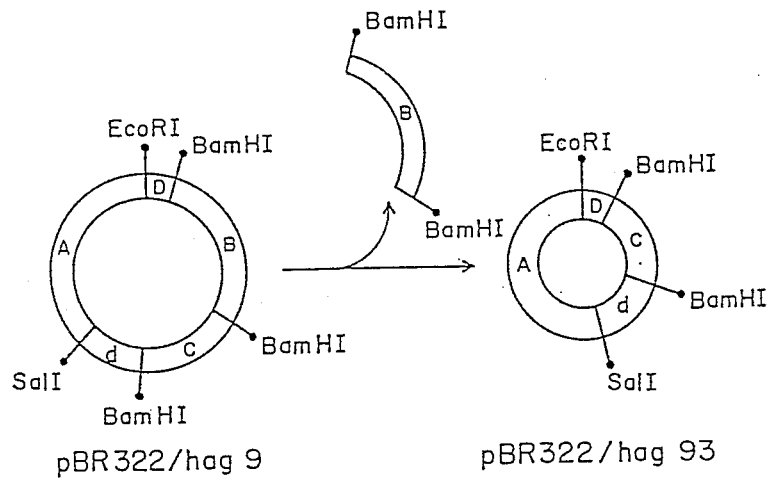
pBR322/hag 9        pBR322/hag 93

Fig.9-1

```
                    GACGGCGAT
            -50               -40
TGAGCCGACGGGGTGGAAACCCAATACGTAA
       -20              -10           -1
TCAACGACTTGCAATATAGGATAACGAATC
  1              10             20              30
  ATGGCACAAGTCATTAATACCAACAGCCTC
  MetAlaGlnValIleAsnThrAsnSerLeu
        40             50             60
TCGCTGATCACTCAAAATAATATCAACAAG
SerLeuIleThrGlnAsnAsnIleAsnLys
       70             80             90
AACCAGTCTGCGCTGTCGAGTTCTATCGAG
AsnGlnSerAlaLeuSerSerSerIleGlu
      100            110            120
CGTCTGTCTTCTGGCTTGCGTATTAACAGC
ArgLeuSerSerGlyLeuArgIleAsnSer
      130            140            150
GCGAAGGATGACGCCAGCGGGTCAGGCATT
AlaLysAspAspAlaAlaGlySerGlyIle
      160            170            180
GCTAACCGTTTCACCTCTAACATTAAAGGC
AlaAsnArgPheThrSerAsnIleLysGly
      190            200            210
CTGACTCAGGCCCCGTAACGCCAACGAC
LeuThrGlnAlaAlaArgAsnAlaAsnAsp
```

```
      220            230.           240
GGTATCTCCGTTGCGCAGACCACCGAAGGC
GlyIleSerValAlaGlnThrThrGluGly
      250            260            270
GCGCTGTCCGAAATCAACAACAACTTACAG
AlaLeuSerGluIleAsnAsnAsnLeuGln
      280            290            300
CGTGTGCGTGAACTGACGGTACAGGCCACT
ArgValArgGluLeuThrValGlnAlaThr
      310            320            330
ACCGGTACTAACTCTGAGTCTGATCTGTCT
ThrGlyThrAsnSerGluSerAspLeuSer
      340            350            360
TCTATCCAGGACGAAATTAAATCCCGTCTG
SerIleGlnAspGluIleLysSerArgLeu
      370            380            390
GATGAAATTGACCGCGTATCTCGGTCAGACC
AspGluIleAspArgValSerGlyGlnThr
      400            410            420
CAGTTCAACGGCGTGAACGTGCTGGCAAAA
GlnPheAsnGlyValAsnValLeuAlaLys
      430            440            450
AATGGCTCCATGAAAATCCAGGTTGGCGCA
AsnGlySerMetLysIleGlnValGlyAla
      460            470            480
AATGATAACCAGACTATCACTATCGATCTG
AsnAspAsnGlnThrIleThrIleAspLeu
```

Fig. 9-2

```
         490              500              510
AAGCAGATTGATGCTAAAACTCTTGGCCTT
LysGlnIleAspAlaLysThrLeuGlyLeu
         520              530              540
GATGGTTTTAGCGTTAAAAATAACGATACA
AspGlyPheSerValLysAsnAsnAspThr
         550              560              570
GTTACCACTAGTGCCTCCAGTAAACTGCTTTT
ValThrThrSerAlaProValThrAlaPhe
         580              590              600
GGTGCTACCACCACAAAACAATATTAAACTT
GlyAlaThrThrThrAsnAsnIleLysLeu
         610              620              630
ACTGGAATTACCCTTTCTACGGAAGCAGCC
ThrGlyIleThrLeuSerThrGluAlaAla
         640              650              660
ACTGATACTGGCGCGGAACTAACCCAGCTTCA
ThrAspThrGlyGlyAsnProAlaSer
         670              680              690
ATTGAGGGTGTTTATACTGATAATGGTAAT
IleGluGlyValTyrThrAspAsnGlyAsn
         700              710              720
GATTACTATGCCGAAAATCACCGGTGGTGAT
AspTyrTyrAlaLysIleThrGlyGlyAsp
         730              740              750
AACGATGGGAAGTATTACGCAGTAACAGTT
AsnAspGlyLysTyrTyrAlaValThrVal
         760              770              780
GCTAATGATGGTACAGTGGACAATGGCGACT
AlaAsnAspGlyThrValThrMetAlaThr
         790              800              810
GGAGCAACGGCAAATGCAACTGTAACTGAT
GlyAlaThrAlaAsnAlaThrValThrAsp
         820              830              840
GCAAATACTAACTAAAGCTACAACTATCACT
AlaAsnThrThrLysAlaThrThrIleThr
         850              860              870
TCAGGCGGTACACCTGTTCAGATTGATAAT
SerGlyGlyThrProValGlnIleAspAsn
         880              890              900
ACTGCAGGTTCCGCAACTGCCAACCTTGGT
ThrAlaGlySerAlaThrAlaAsnLeuGly
         910              920              930
GCTGTTAGCTTAGTAAAACTGCAGGATTCC
AlaValSerLeuValLysLeuGlnAspSer
         940              950              960
AAGGGTAATGATACCGATACATATGCCTT
LysGlyAsnAspThrAspThrTyrAlaLeu
         970              980              990
AAAGATACAAATGGCAATCTTTACGCTGCG
LysAspThrAsnGlyAsnLeuTyrAlaAla
        1000             1010             1020
GATGTGAATGAAACTACTGGTGCTGTTTCT
AspValAsnGluThrThrGlyAlaValSer
```

Fig.9-3

```
1030              1040              1050
GTTAAAACTATTACCTATACTGACTCTTCC
 ValLysThrIleThrTyrThrAspSerSer
1060              1070              1080
GGTGCCGCCAGTTCTCCAACCGGCGTCAAA
 GlyAlaAlaSerSerProThrAlaValLys
1090              1100              1110
CTGGGCGGAGATGATGGCAAAACAGAAGTG
 LeuGlyGlyAspAspGlyLysThrGluVal
1120              1130              1140
GTCGATATTGATGGTAAAACATACGATTCT
 ValAspIleAspGlyLysThrTyrAspSer
1150              1160              1170
GCCGATTTAAATGGCGGTAATCTGCAAACA
 AlaAspLeuAsnGlyGlyAsnLeuGlnThr
1180              1190              1200
GGTTTGACTGCTGGTGGTGAGGCTCTGACT
 GlyLeuThrAlaGlyGlyGluAlaLeuThr
1210              1220              1230
GCTGTTGCAAATGGTAAAACCACGGATCCG
 AlaValAlaAsnGlyLysThrThrAspPro
1240              1250              1260
CTGAAAGCGCTGGACGATGCTATCGCATCT
 LeuLysAlaLeuAspAspAlaIleAlaSer
1270              1280              1290
GTAGACAAATTCCGTTCTTCCCTCGGTGCG
 ValAspLysPheArgSerSerLeuGlyAla
1300              1310              1320
GTGCAAAACCGTCTCTGGATTCCGCGGTTACC
 ValGlnAsnArgLeuAspSerAlaValThr
1330              1340              1350
AACCTGAACAACACCACTACCAACCTGTCT
 AsnLeuAsnAsnThrThrThrAsnLeuSer
1360              1370              1380
GAAGCGCAGTCCCGTATTCAGGACGCCGAC
 GluAlaGlnSerArgIleGlnAspAlaAsp
1390              1400              1410
TATGCGACCGAAGTGTCCAATATGTCGAAA
 TyrAlaThrGluValSerAsnMetSerLys
1420              1430              1440
GCGCAGATCATCCAGCAGGCCGGTAACTCC
 AlaGlnIleIleGlnGlnAlaGlyAsnSer
1450              1460              1470
GTGTTGGCAAAAGCTAACCAGGTACCGCAG
 ValLeuAlaLysAlaAsnGlnValProGln
1480              1490
CAGGTTCTGTCTCTGCTGCAGGGTTAATCG
 GlnValLeuSerLeuLeuGlnGly***

TTGTAACCTGATTAACTGCCTGAGACTGACGGCA

ACGCCAAATTGCCTGATGCGCTGCGCTTAT

CAGGCCTACAAGTTGAATTGCAATTTATTG

AATTTGCACCCCAGGCCAGTGCTTTAGCGT
T̲
``` a : 0.45 Kbp   b : 0.7 Kbp   c : 0.7 Kbp
d : 2.3 Kbp    e : 2.7 Kbp

H : Hinc II

---> :DNA sequencing

Fig. 14A-1

```
         10         20         30         40         50         60
ATGGCACAAGTCATTAATACCAACAGCCTCTCGCTGATCACTCAAAATATCAACAAG
 M  A  Q  V  I  N  T  N  S  L  S  L  I  T  Q  N  N  I  N  K 70         80         90        100        110        120
AACCAGTCTGCGCTGTCGAGTTCTATCGAGCGTCTTCTGGCTTCGGTATTAACAGC
 N  Q  S  A  L  S  S  S  I  E  R  L  S  S  G  L  R  I  N  S 130        140        150        160        170        180
GCGAAGGATGACGCCAGCGGGTCAGGCGATTGCTAACCGTTTCACCTCTAACATTAAAGGC
 A  K  D  D  A  A  G  Q  A  I  A  N  R  F  T  S  N  I  K  G 190        200        210        220        230        240
CTGACTCAGGCGGCCCGTAACGCCAACGACGGTATCTCCGTTGCGCAGACCACCGAAGGC
 L  T  Q  A  A  R  N  A  N  D  G  I  S  V  A  Q  T  T  E  G 250        260        270        280        290        300
GCGCTCTGCCGAAATCAACAACAACTTACAGCGTGTGCGTGAACTGACGGTACAGGCCACT
 A  L  S  E  I  N  N  N  L  Q  R  V  R  E  L  T  V  Q  A  T 310        320        330        340        350        360
ACCGGTACTAACTCTGAGTCTGATCTGTCTTCTATCCAGGACGAAATTAAATCCCGTCTG
 T  G  T  N  S  E  S  D  L  S  S  I  Q  D  E  I  K  S  R  L
```

Fig.14A-2

```
        370       380       390       400       410       420
GATGAAATTGACCCGTATCTGGTCAGACCCACTTCAACGGCGTGAACGTGCTGGCAAAA
 D  E  I  D  R  V  S  G  Q  T  Q  F  N  G  V  N  V  L  A  K 430       440       450       460       470       480
AATGGCTCCATGAAAATCCAGGTTGGCGCAAATGATAACCAGACTATCACTATCGATCTG
 N  G  S  M  K  I  Q  V  G  A  N  D  N  Q  T  I  T  I  D  L 490       500       510       520       530       540
AAGCAGATTGATGCTAAAACTCTTGGCCTTGATGGTTTTACCGTTAAAAATAACGATACA
 K  Q  I  D  A  K  T  L  G  L  D  G  F  S  V  K  N  N  D  T 550       560       570       580       590       600
GTTACCACTAGTGCTCCAGTAACTGCTTTTGGTGCTACCACCAAGCTTCCCGGGAGATCT
 V  T  T  S  A  P  V  T  A  F  G  A  T  T  K  L  P  G  R  S 610       620       630       640       650       660
GATTTAAATGGCGGTAATCTGCAAACAGGTTTGACTGCTGGTGAGGCTCTGACTGCT
 D  L  N  G  G  N  L  Q  T  G  L  T  A  G  G  E  A  L  T  A 670       680       690       700       710       720
GTTGCAAATGGTAAAACCACGGATCCGCTGAAAGCGCTGGACGATGCTATCGCATCTGTA
 V  A  N  G  K  T  T  D  P  L  K  A  L  D  D  A  I  A  S  V
```

Fig. 14A-3

```
       730        740        750        760        770        780
GACAAAATTCCGTTCTTCCCTCGGTCCGTGCGGTGCAAAACCGTCTGGATTCCGCGGTTACCAAC
 D   K   F   R   S   S   L   G   A   V   Q   N   R   L   D   S   A   V   T   N
       790        800        810        820        830        840
CTGAACAACACCACTACCAACCTGTCTGAAGCGGCAGTCCCCTATTCAGGACGCCGACTAT
 L   N   N   T   T   T   N   L   S   E   A   Q   S   R   I   Q   D   A   D   Y
       850        860        870        880        890        900
GCGACCGAAGTGTCCAATATGTCGAAAGCGGCAGATCATCAGCAGGCCGGTAACTCCGTG
 A   T   E   V   S   N   M   S   K   A   Q   I   I   Q   Q   A   G   N   S   V
       910        920        930        940        950
TTGGCAAAGCTAACCAGGTACCGCAGCAGGTTCTGTCTCTGCTGCAGGGTTAA
 L   A   K   A   N   Q   V   P   Q   Q   V   L   S   L   L   Q   G   *
```

Fig.14B-1

```
         10         20         30         40         50         60
ATGGCACAAGTCATTAATACCAACAGCCTCTCGCTGATCACTCAAAATAATATCAACAAG
 M  A  Q  V  I  N  T  N  S  L  S  L  I  T  Q  N  N  I  N  K 70         80         90        100        110        120
AACCAGTCTGCCCTGTCGAGTTCTATCGAGGCTCTCTCTTCTGGCTTGCGTATTAACAGC
 N  Q  S  A  L  S  S  S  I  E  R  L  S  S  G  L  R  I  N  S 130        140        150        160        170        180
GCGAAGGATGACGCAGGGGTCAGGCGATTGCTAACGTTTCACCTCTAACATTAAAGGC
 A  K  D  D  A  A  G  Q  A  I  A  N  R  F  T  S  N  I  K  G 190        200        210        220        230        240
CTGACTCAGGCGCCCCGTAACGCCAACGACGTATCTCCGTTGCCAGACCACCGAAGGC
 L  T  Q  A  A  R  N  A  N  D  G  I  S  V  A  Q  T  T  E  G 250        260        270        280        290        300
GCGCTGTCCGAAATCAACAACAACTTACAGCGTGTGCGTGAACTGACGGTACAGGCCACT
 A  L  S  E  I  N  N  N  L  Q  R  V  R  E  L  T  V  Q  A  T 310        320        330        340        350        360
ACCGGTACTAACTCTGAGTCTGATCTGTCTTCTATCCAGGACGAAATTAAATCCCGTCTG
 T  G  T  N  S  E  S  D  L  S  S  I  Q  D  E  I  K  S  R  L
```

Fig. 14B-2

```
        370       380       390       400       410       420
GATGAAATTGACCGGCGTATCTGGTCAGACCCAGTTCAACGGGCGTGAACGTGCTGGCAAAA
 D   E   I   D   R   V   S   G   Q   T   Q   F   N   G   V   N   V   L   A   K 430       440       450       460       470       480
AATGGCTCCATGAAAATCCAGGTTGGCGCAAATGATAACCAGACTATCACTATCGATCTG
 N   G   S   M   K   I   Q   V   G   A   N   D   N   Q   T   I   T   I   D   L 490       500       510       520       530       540
AAGCAGATTGATGCTAAAACTCTTGGCCTTGATGGTTTAGCGTTAAAAATAACGATACA
 K   Q   I   D   A   K   T   L   G   L   D   G   F   S   V   K   N   N   D   T 550       560       570       580       590       600
GTTACCACTAGTGCCTCCAGTAACTGCTTTTGGTGCTACCACCACAAACAATATTAAACTT
 V   T   T   S   A   P   V   T   A   F   G   A   T   T   T   N   N   I   K   L 610       620       630       640       650       660
ACTGAGATCTCCCGGGCAAGCTTTGCTTAAAGATACAAATGGCAATCTTTACGCTGCGGAT
 T   E   I   S   R   E   A   L   L   K   D   T   N   G   N   L   Y   A   A   D 670       680       690       700       710       720
GTGAATGAAACTACTGGTGCTGTTTCTGTTTAAAACTATTACCTATACTGACTCTTCCGGT
 V   N   E   T   T   G   A   V   S   V   K   T   I   T   Y   T   D   S   S   G
```

Fig.14B-3

```
        730       740       750       760       770       780
GCCGCCAGTTCTCCAACCGGGTCAAACTGGGGCGGAGATGATGCCAAAACAGAAGTGGTC
 A  A  S  S  P  T  A  V  K  L  G  G  D  D  K  T  E  V  V 790       800       810       820       830       840
GATATTGATGGTAAAACATACGATTCTGCCGATTTAAATGGCGGTAATCTGCAAACAGGT
 D  I  D  G  K  T  Y  D  S  A  D  L  N  G  G  N  L  Q  T  G 850       860       870       880       890       900
TTGACTGCTGGTGGTGAGGCTCTGACTGCTGTTGCAAATGGTAAAACCACGGATCCGCTG
 L  T  A  G  G  E  A  L  T  A  V  A  N  G  K  T  T  D  P  L 910       920       930       940       950       960
AAAGGGCTGGACGATGCTATCGCATCTGTAGACAAATTCCGTTCTTCCCTCGGTGCGGTG
 K  A  L  D  D  A  I  A  S  V  D  K  F  R  S  S  L  G  A  V 970       980       990      1000      1010      1020
CAAAACCGTCTGGATTCCGCGGCTTACCAACCTGAACAACCACTACCAACCTGTCTGAA
 Q  N  R  L  D  S  A  V  T  N  L  N  N  T  T  N  L  S  E 1030      1040      1050      1060      1070      1080
GCGCAGTCCCGTATTCAGGACGCCGACTATGCCGAAGTGTCCAATATGTCGAAAGCG
 A  Q  S  R  I  Q  D  A  D  Y  A  T  E  V  S  N  M  S  K  A
```

Fig. 14B-4

```
         1090      1100      1110      1120      1130      1140
CAGATCATCCAGCAGGCCGGTAACTCCGTGTTGGCAAAAGCTAACCAGGTACCGCAGCAG
 Q  I  I  Q  Q  A  G  N  S  V  L  A  K  A  N  Q  V  P  Q  Q
         1150      1160
GTTCTGTCTCTGCCTGCAGGGTTAA
 V  L  S  L  L  Q  G  *
```

Fig.14C-1

```
         10         20         30         40         50         60
ATGGCACAAGTCATTAATACCAACAGCCTCTCGCTGATCACTCAAAATAATATCAACAAG
 M  A  Q  V  I  N  T  N  S  L  S  L  I  T  Q  N  N  I  N  K 70         80         90        100        110        120
AACCAGTCTGCGCTGTCGAGTTCTATCGAGGTCTCTTCTGGCTTGCGTATTAACAGC
 N  Q  S  A  L  S  S  S  I  E  R  L  S  S  G  L  R  I  N  S 130        140        150        160        170        180
GCGAAGGATGACGCAGCGGGTCAGGGCGATTGCTAACCGTTTCACCTCTAACATTAAAGGC
 A  K  D  D  A  A  G  Q  A  I  A  N  R  F  T  S  N  I  K  G 190        200        210        220        230        240
CTGACTCAGGCGCCCCTAACGCCAACGACGGTATCTCCGTTGCCAGACCACCGAAGGC
 L  T  Q  A  A  R  N  A  N  D  G  I  S  V  A  Q  T  T  E  G 250        260        270        280        290        300
GCCCTGTCCGAAATCAACAACAACTTACAGCGTCTGCGTGAACTGACGGTACAGGCCACT
 A  L  S  E  I  N  N  N  L  Q  R  V  R  E  L  T  V  Q  A  T 310        320        330        340        350        360
ACCCGTACTAACTCTGAGTCTGATCTGTCTTCTATCCAGGACGAAATTAAATCCCGTCTG
 T  G  T  N  S  E  S  D  L  S  S  I  Q  D  E  I  K  S  R  L
```

Fig.14C-2

```
          370        380        390        400        410        420
GATGAAATTGACCCGGTATCTGCTCAGACCCAGTTCAACGGGCCGTGAACGTGCTGGCAAAA
 D   E   I   D   R   V   S   G   Q   T   Q   F   N   G   V   N   V   L   A   K 430        440        450        460        470        480
AATGGCTCCATGAAAAATCCAGGTTGGCGCAAATGATAACCAGACTATCACTATCGATCTG
 N   G   S   M   K   I   Q   V   G   A   N   D   N   Q   T   I   T   I   D   L 490        500        510        520        530        540
AAGCAGATTGATGCTAAAACTCTTGGCCTTGATGGTTTTAGCGTTAAAAATAACGATACA
 K   Q   I   D   A   K   T   L   G   L   D   G   F   S   V   K   N   N   D   T 550        560        570        580        590        600
GTTACCACTAGTGCTCCAGTAACTGCTTTTGGTGCTACCACCACAACAAACAATATTAAACTT
 V   T   S   A   P   V   T   A   F   G   A   T   T   T   N   N   I   K   L 610        620        630        640        650        660
ACTGGAATTACCCTTTCTACGGAAGCAGCACTGATACTGGCGGAACTAACCCAGAAGCT
 T   G   I   T   L   S   T   E   A   A   T   D   T   G   G   T   N   P   E   A 670        680        690        700        710        720
TCCCGGGAGATCTACGCTGCGGCCATGTGAATGAAAACTACTGGTGCTGTTTCTGTTAAAACT
 S   R   E   I   Y   A   A   D   V   N   E   T   T   G   A   V   S   V   K   T
```

Fig.14C-3

```
      730           740           750           760           770           780
ATTACCTATACTGACTCTTCCGGTGCCGCCAGTTCTCCAACCGGTCAAACTGGGCGGA
 I  T  Y  T  D  S  S  G  A  A  S  P  T  A  V  K  L  G  G 790           800           810           820           830           840
GATGATGGCAAAACAGAAGTGGTCGATATTGATGGTAAAACATACGATTCTGCCGATTTA
 D  D  G  K  T  E  V  V  D  I  D  G  K  T  Y  D  S  A  D  L 850           860           870           880           890           900
AATGGCGGTAATCTGCAAACAGGTTTGACTGCTGGTGGTGAGGCTCTGACTGCTGTTGCA
 N  G  G  N  L  Q  T  G  L  T  A  G  G  E  A  L  T  A  V  A 910           920           930           940           950           960
AATGGTAAAACCACGGATCCGCTGAAAGCGCTGGACGATGCTATCGCATCTGTAGACAAA
 N  G  K  T  T  D  P  L  K  A  L  D  D  A  I  A  S  V  D  K 970           980           990          1000          1010          1020
TTCCGTTCTTCCCTCCGGTTGCGGTGCAAAACCGTCTGGATTCCGCGGTTACCAACCTGAAC
 F  R  S  S  L  G  A  V  Q  N  R  L  D  S  A  V  T  N  L  N 1030          1040          1050          1060          1070          1080
AACACCACTACCAACCTGTCTGAAGCGCAGTCCCGTATTCAGGACGCCGACTATGCGACC
 N  T  T  N  L  S  E  A  Q  S  R  I  Q  D  A  D  Y  A  T
```

Fig. 14C-4

```
     1090      1100      1110      1120      1130      1140
GAAGTGTCCAATATGTCGAAAGCGGCAGATCATCCAGCAGCCGGTAACTCCGTGTTGGCA
  E  V  S  N  M  S  K  A  Q  I  I  Q  Q  A  G  N  S  V  L  A
     1150      1160      1170      1180      1190
AAAGCTAACCAGGTACCGCAGCCAGGTTCTCTGTCTCTGCTGCAGGGGTTAA
  K  A  N  Q  V  P  Q  Q  V  L  S  L  L  Q  G  *
```

Fig.14D-1

```
         10        20        30        40        50        60
ATGGCACAAGTCATTAATACCAACAGCCTCTCGCTGATCACTCAAAATAATATCAACAAG
 M  A  Q  V  I  N  T  N  S  L  S  L  I  T  Q  N  N  I  N  K 70        80        90       100       110       120
AACCAGTCTGCGCTGTCGAGTTCTATCGAGCGGTCTCTGTCTTCTGGCTTGCGTATTAACAGC
 N  Q  S  A  L  S  S  S  I  E  R  L  S  S  G  L  R  I  N  S 130       140       150       160       170       180
GCGAAGGATGACGCAGCGGTCAGGCGATTGCTAACCGTTTCACCTCTAACATTAAAGGC
 A  K  D  D  A  A  G  Q  A  L  A  N  R  F  T  S  N  I  K  G 190       200       210       220       230       240
CTGACTCAGGCGGCCCGTAACGCCAACGACGGTATCTCCGTTGCCCAGACCACCGAAGGC
 L  T  Q  A  A  R  N  A  N  D  G  I  S  V  A  Q  T  T  E  G 250       260       270       280       290       300
GCGCTGTCCGAAATCAACAACAACTTACAGCGTGTGCGTGAACTGACGGTACAGGCCACT
 A  L  S  E  I  N  N  N  L  Q  R  V  R  E  L  T  V  Q  A  T 310       320       330       340       350       360
ACCGGTACTAACTCTGAGTCTGATCTGTCTTCTATCCAGGACGAAATTAAATCCCGTCTG
 T  G  T  N  S  E  S  D  L  S  S  I  Q  D  E  I  K  S  R  L
```

Fig.14D-2

```
       370       380       390       400       410       420
GATGAAATTGACCGCGTATCTGGTCAGACCCAGTTCAACGGGCGTGAACGTGCTGGCAAAA
 D   E   I   D   R   V   S   G   Q   T   Q   F   N   G   V   N   V   L   A   K 430       440       450       460       470       480
AATGGCTCCATGAAAATCCAGGTTGGCGCAAATGATAACCAGACTATCACTATCGATCTG
 N   G   S   M   K   I   Q   V   G   A   N   D   N   Q   T   I   T   I   D   L 490       500       510       520       530       540
AAGCAGATTGATGCTAAAACTCTTGGCCTTGATGGTTTTAGCGTTAAAAATAACGATACA
 K   Q   I   D   A   K   T   L   G   L   D   G   F   S   V   K   N   N   D   T 550       560       570       580       590       600
GTTACCACTAGTGCCTCCAGTAACTGCTTTTGGTGCTACCACAAACAATATTAAACTT
 V   T   T   S   A   P   V   T   A   F   G   A   T   T   N   N   I   K   L 610       620       630       640       650       660
ACTGGAATTACCCTTTCTACGGAAGCAGCCACTGAGATCTCCCGGGAAGCTTCTGACTCT
 T   G   I   T   L   S   T   E   A   A   T   E   I   S   R   E   A   S   D   S 670       680       690       700       710       720
TCCGGTGCCGCCAGTTCTCCAACGGGTCAAACTGGGCGAGATGATGGCAAAACAGAA
 S   G   A   A   S   S   P   T   A   V   K   L   G   G   D   D   G   K   T   E
```

Fig.14D-3

```
      730         740         750         760         770         780
GTGGTCGATATTGATGGTAAAACATACGATTCTGCCGATTTAAATGGCGGTAATCTGCAA
 V  V  D  I  D  G  K  T  Y  D  S  A  D  L  N  G  G  N  L  Q 790         800         810         820         830         840
ACAGGTTTGACTGCCTGGTGGTGAGGCTCTGACTGCTGTTGCAAATGGTAAAACCACGGAT
 T  G  L  T  A  G  G  E  A  L  T  A  V  A  N  G  K  T  T  D 850         860         870         880         890         900
CCGGCTCAAAAGCGCTGGACGATGCTATCGCATCTGTAGACAAATTCCGTTCTTCCCTCGGT
 P  L  K  A  L  D  D  A  I  A  S  V  D  K  F  R  S  S  L  G 910         920         930         940         950         960
GCGGTGCAAAACCGGCTCTGGATTCCGCGGTTACCAACCTGAACAACACCACTACCAACCTG
 A  V  Q  N  R  L  D  S  A  V  T  N  L  N  N  T  T  T  N  L 970         980         990        1000        1010        1020
TCTGAAGCGCAGTCCCGTATTCAGGACGCCGACTATGCGGACCGAAGTGTCCAATATGTCG
 S  E  A  Q  S  R  I  Q  D  A  D  Y  A  T  E  V  S  N  M  S 1030        1040        1050        1060        1070        1080
AAAGGCCAGATCATCCAGCAGGCCGGTAACTCCGTGTTGGCAAAAGCTAACCAGGTACCG
 K  A  Q  I  I  Q  Q  A  G  N  S  V  L  A  K  A  N  Q  V  P 1090        1100        1110
CAGCAGGTTCTGTCTCTGCTGCAGGGGTTAA
 Q  Q  V  L  S  L  L  Q  G  *
```

Fig.15A-1

```
         10          20          30          40          50          60
ATGGCACAAGTCATTAATACCAACAGCCCTCTCGCTGATCACTCAAAATATCAACAAG
 M  A  Q  V  I  N  T  N  S  L  S  L  I  T  Q  N  N  I  N  K 70          80          90         100         110         120
AACCAGTCTGCGCTGTCGAGTTCTATCGAGCGTCTGTCTTCGGCTTGCGTATTAACAGC
 N  Q  S  A  L  S  S  S  I  E  R  L  S  S  G  L  R  I  N  S 130         140         150         160         170         180
GCGAAGGATGACGCCAGCGGGTCAGGCGATTGCTAACCGTTTCACCTCTAACATTAAAGGC
 A  K  D  D  A  A  G  Q  A  I  A  N  R  F  T  S  N  I  K  G 190         200         210         220         230         240
CTGACTCAGGCGGGCCCGTAACGCCAACGACGGTATCTCCGTTGCCAGACCACCGAAGGC
 L  T  Q  A  A  R  N  A  N  D  G  I  S  V  A  Q  T  T  E  G 250         260         270         280         290         300
GCGCTGTCCGAAATCAACAACAACTTACAGCGTGTGCGTGAACTGACGGTACAGGCCACT
 A  L  S  E  I  N  N  N  L  Q  R  V  R  E  L  T  V  Q  A  T 310         320         330         340         350         360
ACCGGTACTAACTCTGAGTCTGATCTGTCTTCTATCCAGGACGAAATTAAATCCCGTCTG
 T  G  T  N  S  E  S  D  L  S  S  I  Q  D  E  I  K  S  R  L
```

Fig.15A-2

```
       370       380       390       400       410       420
GATGAAATTGACCGGCGTATCTGGTCAGACCCAGTTCAACGGCGTGAACGTGCTGGCAAAA
 D   E   I   D   R   V   S   G   Q   T   Q   F   N   G   V   N   V   L   A   K 430       440       450       460       470       480
AATGGCTCCATGAAATCCAGGTTGGCGCAAATGATAACCAGACTATCACTATCGATCTG
 N   G   S   M   K   I   Q   V   G   A   N   D   N   Q   T   I   T   I   D   L 490       500       510       520       530       540
AAGCAGATTGATGCTAAAACTCTTGGCCTTGATGGTTTTAGCGTTAAAAATAACGATACA
 K   Q   I   D   A   K   T   L   G   L   D   G   F   S   V   K   N   N   D   T 550       560       570       580       590       600
GTTACCACTAGTGCTCCAGTAACTGCTTTTGGTGCTACCACCACAAACAATATTAAACTT
 V   T   T   S   A   P   V   T   A   F   G   A   T   T   T   N   N   I   K   L 610       620       630       640       650       660
ACTGGAATTACCCTTTCTACGGAAGCAGAAGCTTCCCGGGAGATCTGTGCTGTTAGCTTA
 T   G   I   T   L   S   T   E   A   E   A   S   R   E   I   C   A   V   S   L 670       680       690       700       710       720
GTAAAACTGCAGGATTCCAAGGGTAATGATACCGATACATATGCGCTTAAAGATACAAAT
 V   K   L   Q   D   S   K   G   N   D   T   D   T   Y   A   L   K   D   T   N
```

Fig.15A-3

```
        730       740       750       760       770       780
GGCAATCTTTACGCTGCGGATGTGAATGAAACTACTGGTGCTGTTTCTGTTAAAACTATT
 G  N  L  Y  A  A  D  V  N  E  T  T  G  A  V  S  V  K  T  I 790       800       810       820       830       840
ACCTATACTGACTCTTCCGGTCCCGCCCCAGTTCTCCAACCGGGTCAAACTGGGCGGAGAT
 T  Y  T  D  S  S  G  A  A  S  P  T  A  V  K  L  G  G  D 850       860       870       880       890       900
GATGGCAAAACAGAAGTGGTCGATATTGATGGTAAAACATACGATTCTGCCGATTTAAAT
 D  G  K  T  E  V  V  D  I  D  G  K  T  Y  D  S  A  D  L  N 910       920       930       940       950       960
GGGCGTAATCTGCAAACAGGTTTGACTGCTGGTGGTGAGCCTCTGACTGCTGTTGCAAAT
 G  G  N  L  Q  T  G  L  T  A  G  G  E  A  L  T  A  V  A  N 970       980       990      1000      1010      1020
GGTAAAACCACGGATCCGCTGAAAGCGCTGGACGATGCTATCGCCATCTGTAGACAAATTC
 G  K  T  T  D  P  L  K  A  L  D  D  A  I  A  S  V  D  K  F 1030      1040      1050      1060      1070      1080
CGTTCTCCCTCGGTGCGGTGCAAAACCGTCTGGATTCCGGGTTACCAACCTGAACAAC
 R  S  S  L  G  A  V  Q  N  R  L  D  S  A  V  T  N  L  N  N
```

Fig.15A-4

```
        1090       1100       1110       1120       1130       1140
ACCACTACCAACCTGTCTGAAGCCCAGTCCCGTATTCAGGACGCCGACTATGCCGACCGAA
 T  T  T  N  L  S  E  A  Q  S  R  I  Q  D  A  D  Y  A  T  E
        1150       1160       1170       1180       1190       1200
GTGTCCAATATGTCGAAAGCGCAGATCATCCAGCAGGCCGGTAACTCCGTGTTGGCAAAA
 V  S  N  M  S  K  A  Q  I  I  Q  Q  A  G  N  S  V  L  A  K
        1210       1220       1230       1240
GCTAACCAGGTACCGCAGCAGGTTCTGTCTCTGCTGCAGGGGTTAA
 A  N  Q  V  P  Q  Q  V  L  S  L  L  Q  G  *
```

Fig.15B-1

```
         10         20         30         40         50         60
ATGGCACAAGTCATTAATACCAACAGCCTCTCGCTGATCACTCAAAATAATATCAACAAG
 M  A  Q  V  I  N  T  N  S  L  S  L  I  T  Q  N  N  I  N  K 70         80         90        100        110        120
AACCAGTCTGCGCTGTCGAGTTCTATCGAGCGTCTTCTCGGCTTGCCTATTAACAGC
 N  Q  S  A  L  S  S  S  I  E  R  L  S  S  G  L  R  I  N  S 130        140        150        160        170        180
GCGAAGGATGACGCAGGCGTCAGGCGATTGCTAACCGTTTCACCTCTAACATTAAAGGC
 A  K  D  D  A  A  G  Q  A  I  A  N  R  F  T  S  N  I  K  G 190        200        210        220        230        240
CTGACTCAGGCGGCCCGTAACGCCAACGACGGTATCTCCGTTGCGCAGACCACCGAAGGC
 L  T  Q  A  A  R  N  A  N  D  G  I  S  V  A  Q  T  T  E  G 250        260        270        280        290        300
GCGCTGTCCGAAATCAACAACAACTTACAGCGTGTCCGTGAACTGACGGTACAGGCCACT
 A  L  S  E  I  N  N  N  L  Q  R  V  R  E  L  T  V  Q  A  T 310        320        330        340        350        360
ACCGGTACTAACTCTGAGTCTGATCTGTCTTCTATCCAGGACGAAATTAAATCCCGTCTG
 T  G  T  N  S  E  S  D  L  S  S  I  Q  D  E  I  K  S  R  L
```

Fig.15B-2

```
        370       380       390       400       410       420
GATGAAATTGACCGGGTATCTGGTCAGACCCAGTTCAACGGCCTGAACGTGCTGGCAAAA
 D  E  I  D  R  V  S  G  Q  T  Q  F  N  G  V  N  V  L  A  K 430       440       450       460       470       480
AATGGCTCCATGAAAATCCAGGTTGGCGCAAATGATAACCAGACTATCACTATCGATCTG
 N  G  S  M  K  I  Q  V  G  A  N  D  N  Q  T  I  T  I  D  L 490       500       510       520       530       540
AAGCAGATTGATGCTAAAACTCTTGGCCTTGATGGTTTAAAAATAACGATACA
 K  Q  I  D  A  K  T  L  G  L  D  G  F  S  V  K  N  D  T 550       560       570       580       590       600
GTTACCACTAGTGCTCCAGTAACTGCTTTTGGTGCTACCACCACAAACAATATTAAACTT
 V  T  T  S  A  P  V  T  A  F  G  A  T  T  T  N  N  I  K  L 610       620       630       640       650       660
ACTGGAATTACCCTTTCTACGGAAGCAGCCACTGATACTGGCCCGAACTAACCCAGCTTCA
 T  G  I  T  L  S  T  E  A  A  T  D  T  G  G  T  N  P  A  S 670       680       690       700       710       720
ATTGAGGGTGTTTATACTGATAATGGTAATGATTACTATGCGAAAATCACCGGTGGTGAT
 I  E  G  V  Y  T  D  N  G  N  D  Y  Y  A  K  I  T  G  G  D
```

Fig.15B-3

```
                  730            740            750            760            770            780
            AACGATGGAAGTATAGATCTCCCGGGAAGCTTAGCTTAGTAAAACTGCAGGATTCCAAG
             N  D  G  K  Y  R  S  P  G  K  L  S  L  V  K  L  Q  D  S  K 790            800            810            820            830            840
            GGTAATGATACCGATACATATGGCTTAAAGATACAAATGGCAATCTTTACGCTGCCGAT
             G  N  D  T  D  T  Y  A  L  K  D  T  N  G  N  L  Y  A  A  D 850            860            870            880            890            900
            GTGAATGAAACTACTGGTGCTGTTTCTGTTAAAACTATTACCTATACTGACTCTTCCGGT
             V  N  E  T  T  G  A  V  S  V  K  T  I  T  Y  T  D  S  S  G 910            920            930            940            950            960
            GCCGCCAGTTCTCCAACCGCGGTCAAACTGGGCCCGAGATGATGGCAAAACAGAAGTGGTC
             A  A  S  S  P  T  A  V  K  L  G  G  D  D  G  K  T  E  V  V 970            980            990           1000           1010           1020
            GATATTGATGGTAAAACATACGATTCTGCCGATTTAAATGGCGGTAATCTGCAAACAGGT
             D  I  D  G  K  T  Y  D  S  A  D  L  N  G  G  N  L  Q  T  G 1030           1040           1050           1060           1070           1080
            TTGACTGCTCGTGGTGAGGCTCTCGACTGCTCTTCCAAATGGTAAAACCACGGATCCGCTG
             L  T  A  G  G  E  A  L  T  A  V  A  N  G  K  T  T  D  P  L
```

Fig.15B-4

```
                              1090                1100                1110                1120                1130                1140
                              AAAGGCGCTGGACGATGCTATCGGCATCTGTAGACAAATTCCGTTCTTCCCTTCGGTGCGGGTG
                              K   A   L   D   D   A   I   A   S   V   D   K   F   R   S   S   L   G   A   V 1150                1160                1170                1180                1190                1200
                              CAAAACCGTCTGGATTCCGGGGTTACCAACCTGAACAACACCACTACCAACCTGTCTGAA
                              Q   N   R   L   D   S   A   V   T   N   L   N   N   T   T   T   N   L   S   E 1210                1220                1230                1240                1250                1260
                              GCGCAGTCCCGTATTCAGGACGCCGACTATGCGACCGAAGTGTCCAATATGTCGAAAGCG
                              A   Q   S   R   I   Q   D   A   D   Y   A   T   E   V   S   N   M   S   K   A 1270                1280                1290                1300                1310                1320
                              CAGATCATCCAGCAGGCCCGTAACTCCGTGTTGGCAAAAGCTAACCAGGTACCGCAGCAG
                              Q   I   I   Q   Q   A   G   N   S   V   L   A   K   A   N   Q   V   P   Q   Q 1330                1340
                              GTTCTGTCTCTGCTGCAGGGTTAA
                              V   L   S   L   L   Q   G   *
```

Fig.15C-1

```
          10         20         30         40         50         60
ATGGCACAAGTCATTAATACCAACAGCCTCTCGCTGATCACTCAAAATAATATCAACAAG
 M  A  Q  V  I  N  T  N  S  L  S  L  I  T  Q  N  N  I  N  K 70         80         90        100        110        120
AACCAGTCTGCGCTGTCGAGTTCTATCGAGCGTCTGTCTTCTGGCTTGCGTATTAACAGC
 N  Q  S  A  L  S  S  S  I  E  R  L  S  S  G  L  R  I  N  S 130        140        150        160        170        180
GCGAAGGATGACGCAGCGGGTCAGGCGATTGCTAACCGTTTCACCTCTAACATTAAAGGC
 A  K  D  D  A  A  G  Q  A  I  A  N  R  F  T  S  N  I  K  G 190        200        210        220        230        240
CTGACTCAGGCGGCCCGTAACGCCAACGACGGTATCTCCGTTGCGCAGACCACCGAAGGC
 L  T  Q  A  A  R  N  A  N  D  G  I  S  V  A  Q  T  T  E  G 250        260        270        280        290        300
GCGCTGTCCGAAATCAACAACAACTTACAGCGTGTGCGTGAACTGACGGTACAGGCCACT
 A  L  S  E  I  N  N  N  L  Q  R  V  R  E  L  T  V  Q  A  T 310        320        330        340        350        360
ACCCGGTACTAACTCTGAGTCTGATCTGTCTTCTATCCAGGACGAAATTAAATCCCGTCTG
 T  G  T  N  S  E  S  D  L  S  S  I  Q  D  E  I  K  S  R  L
```

Fig.15C-2

```
       370       380       390       400       410       420
CATGAAATTGACCCGTGTATCTGGTCAGACCCAGTTCAACGGGCGTGAACGTGCTGGCAAAA
 D  E  I  D  R  V  S  G  Q  T  Q  F  N  G  V  N  V  L  A  K 430       440       450       460       470       480
AATGGCTCCATGAAAATCCAGGTTGGCGCAAATGATAACCAGACTATCACTATCGATCTG
 N  G  S  M  K  I  Q  V  G  A  N  D  N  Q  T  I  T  I  D  L 490       500       510       520       530       540
AAGCAGATTGATGCTAAAACTCTTGGCCTTGATGGTTTTAGCGTTAAAAATAACGATACA
 K  Q  I  D  A  K  T  L  G  L  D  G  F  S  V  K  N  N  D  T 550       560       570       580       590       600
GTTACCACTAGTGCTCCAGTAACTGCTTTTGGTGCTACCACAACAAACAATATTAAACTT
 V  T  T  S  A  P  V  T  A  F  G  A  T  T  T  N  N  I  K  L 610       620       630       640       650       660
ACTGGAATTACCCTTTCTACGGAAGCAGCCACTGATACTGGCGGAACTAACCCAGCTTCA
 T  G  I  T  L  S  T  E  A  A  T  D  T  G  G  T  N  P  A  S 670       680       690       700       710       720
AAGATCTCCCGGGAAGCTTGCTGTGTTAGCTTAGTAAAACTGCAGGATTCCAAGGGTAAT
 K  I  S  R  E  A  C  A  V  S  L  V  K  L  Q  D  S  K  G  N
```

Fig.15C-3

```
       730          740          750          760          770          780
GATACCGATACATATGCGGCTTAAAGATACAAATGGCAATCTTTACGCTGCCGATCTGAAT
 D  T  D  T  Y  A  L  K  D  T  N  G  N  L  Y  A  A  D  V  N 790          800          810          820          830          840
GAAACTACTGGTGCTCTGTTTCTGTTAAAACTATTACCTATACTGACTCTTCCGGTGCCGCC
 E  T  T  G  A  V  S  V  K  T  I  T  Y  T  D  S  S  G  A  A 850          860          870          880          890          900
AGTTCTCCAACCGCGGTCAAACTGGGCGGCGAGATGATGGCAAAACAGAAGTGGTCGATATT
 S  S  P  T  A  V  K  L  G  G  D  D  G  K  T  E  V  V  D  I 910          920          930          940          950          960
GATGGTAAAACATACGATTCTGCCGATTTAAATGGCGGTAATCTGCAAACAGGTTTGACT
 D  G  K  T  Y  D  S  A  D  L  N  G  G  N  L  Q  T  G  L  T 970          980          990         1000         1010         1020
GCTGGTGTGAGGCTCTGACTGCTCTGTTGCAAATGGTAAACCACGGATCCGCTGAAAGCG
 A  G  G  E  A  L  T  A  V  A  N  G  K  T  T  D  P  L  K  A 1030         1040         1050         1060         1070         1080
CTGGACGATGCTATCCGATCTGTAGACAAATTCCGTTCTTCCCTCCGGTGCCGGTGCAAAAC
 L  D  D  A  I  A  S  V  D  K  F  R  S  S  L  G  A  V  Q  N
```

Fig.15C-4

```
      1090       1100       1110       1120       1130       1140
CGTCTGGATTCCCGGTTACCAACCTGAACAACACCACTACCAACCTGTCTGAAGCGCAG
 R  L  D  S  A  V  T  N  L  N  N  T  T  T  N  L  S  E  A  Q 1150       1160       1170       1180       1190       1200
TCCCGTATTCAGGACCCGACTATGCCGACGAAGTGTCCAATATGTCGAAAGCGCAGATC
 S  R  I  Q  D  A  D  Y  A  T  E  V  S  N  M  S  K  A  Q  I 1210       1220       1230       1240       1250       1260
ATCCAGCAGGCCCGTAACTCCGTGTTGGCAAAAGCTAACCAGGTACCGCAGCAGGTTCTG
 I  Q  Q  A  G  N  S  V  L  A  K  A  N  Q  V  P  Q  Q  V  L 1270       1280
TCTCTGCTGCAGGGTTAA
 S  L  L  Q  G  *
```

DNA ENCODING FLAGELLIN AND VECTOR HAVING THE SAME

BACKGROUND OF THE INVENTION

1. Field of the Invention

This invention relates to a gene encoding flagellin and an excretion vector having a gene encoding flagellin or a part of said gene.

2. Prior Art

A recent development of gene engineering made it easier that a gene encoding certain peptide is inserted into a vector and then the vector is introduced into bacteria such as *Escherichia coli* to give a large amount of the peptide. However, since a peptide expressed in bacteria is accumulated therein, growth of the bacteria is inhibited by the expressed peptide and production of the peptide is restricted by negative-feedback through excess production of the peptide. In order to recover the peptide, it is necessary to collect and destroy the bacteria, and to purify the peptide from the cell debris. It contains a lot of impurities, some of which are pathogenic to human beings, so that it is hard to recover the pure peptide therefrom.

Peptides composing cell membrane, secreted peptides and so on are synthesized as pro-peptides having signal sequence at their N-terminal, which is necessary for their passing through inner or outer membrane. The pro-peptide, from which the signal sequence is cut off by peptidase in the membrane in passing through the membrane, becomes a mature peptide to show its original activity and function.

So as to remove the difficulty in refining the target peptide accumulated in cells and improve productivity of the target peptide, it has been attempted to make cells secrete a target peptide outside by utilizing the natural secretion system of the cell as noted above, for example, secretion of β-lactamase of *Escherichia coli* by a secretion vector carrying promoter and DNA encoding signal sequence of α-amylase of *Bacillus subtilis* (J. Biochem. 95, 87-93 (1984)), secretion of mouse IFN-β by the same vector system as noted above (Gene 34, 1-8 (1985)) and secretion of human IFN-α by a secretion vector carrying a promoter and DNA encoding signal sequence of alkaline phosphatase of *Escherichia coli* (J. Biochem. 97, 1429-1436 (1985)).

Other than the secretion systems as mentioned above, an excretion system is a well known mechanism so that a peptide synthesized in a cell goes out of the cell, for example, flagellin composing flagella of bacteria is excreted outside by this excretion system. In the excretion system, differing from the secretion system, a peptide synthesized in a cell having no signal sequence is excreted out and presents its function without digestion by peptidase (J. Bacteriol. 159, 1056-1059 (1984)). The gene encoding flagellin of *E. coli* is called "hag gene", which has already been cloned in pBR322 and phage λ (Abstracts of the 57th annual meeting of Japanese society of genetics, 63 (1985); J. Bacterial. 130, 736-745 (1977)). Though its partial DNA sequence was analyzed (J. Bacterial. 155, 74-81 (1983)), the whole DNA sequence has not yet been determined.

A secretion of peptide depends upon a type of a secretion vector, that is, a certain type of vector carrying a certain promoter and DNA sequence encoding signal peptide can be used in secretion of only a few kinds of peptides but not all kinds of peptides.

The hag gene encoding flagellin of *E. coli* has already been cloned and its partial sequence has been determined but its whole sequence has not yet been determined. It has not been suggested at all that an excretion system of flagellin can be utilized in production of a target peptide outside of a cell. Moreover, an excretion vector carrying the hag gene has not yet been constructed. The elucidation of the whole sequence of the hag gene makes it easier to construct such a vector.

Now, even if a target peptide is secreted in a broth by utilizing a secretion vector, it is fairly difficult to recover and refine the peptide from the broth. However, if a target peptide is excreted as a fused peptide with flagellin and composes flagella to become insoluble, it becomes easier to recover the peptide.

SUMMARY

The whole sequence of DNA coding for flagellin of *E. coli* (hag gene) cloned in phage λ as noted above was determined by the present inventors. The hag gene is introduced into pBR322 and the region of the hag gene concerning the antigenicity of flagella is lacked, into which linkers having suitable restriction sites are inserted. Where the vector that foreign DNA is inserted in the linker is introduced in *E. coli* forming no flagella, the *E. coli* becomes to form flagella and present motility. The flagella comprises flagellin fused with foreign peptide encoded by the foreign DNA. Namely, the foreign peptide is excreted outside of bacteria. In case that the foreign peptide fused with flagellin is a part concerning the antigenicity of the foreign peptide, the transformant does not present motility on the medium containing the antibody against the foreign peptide. Therefore, this system can be utilized in determination of epitope and preparation of antigen.

BRIEF DESCRIPTION OF THE DRAWINGS

FIG. 1 shows DNA sequence of hag gene encoding flagellin of *E. coli* and amino acid sequence deduced from the DNA sequence. FIG. 4 shows BamHI restriction sites on pBR322/hag9. FIG. 5 shows pBR322/hag93 lacking fragment B of pBR322/hag9.

FIG. 9 shows whole primary structure of hag gene determined by DNA sequencing. FIG. 14 shows sequences of hag gene carried on pFD301, pFD303, pFD306 and pFD307. FIG. 15 shows sequences of hag gene carried on pFD311, pFD313 and pFD315.

DETAILED DESCRIPTION OF THE INVENTION

Figure 2:
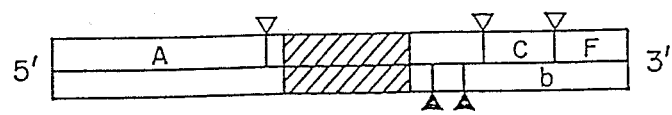
FIG. 2 shows a result of digestion of λ pfla-H2 with EcoRI and Sal$_I$, in which oblique lines indicate a deduced position of DNA fragment carrying hag gene derived from chromosome of *E. coli*.

The present inventors remarked an excretion system of flagellin in investigating a system in which a target peptide is produced outside of a cell. Therefore, the whole base sequence of hag gene encoding flagellin was determined and the gene was inserted into a vector and then the hag gene on the vector was cut or a part of the hag gene on the vector was removed and into the resulting space is inserted linker DNA. Into the linker DNA in the vector is inserted DNA coding for a foreign peptide and the resulting vector is introduced into bacteria. As a result, the foreign peptide is excreted from the bacteria as a fused peptide with flagellin. Under certain condition the excreted peptide forms flagella, which facilitates the recovery of the peptide. Moreover, it may be possible that some foreign peptides which could not be secreted from bacteria by conventional secretion systems are excreted by this excretion system.

The DNA encoding flagellin can be prepared from all kinds of bacteria that have flagella such as E. coli, Bacillus subtilis, Proteus and so on. For example, hag gene encoding flagellin of E. coli is prepared in accordance with the method of Kondoh et al (J. Bacteriol. 130, 736–745 (1977)). However, it is easier to use the hag gene already cloned in pBR322 or λ phage.

The present invention is explained by exemplifying the hag gene but not restricted into the use of the hag gene since all of DNA encoding flagellin can be employed in this invention.

Phage or plasmid carrying the hag gene is introduced into bacteria that cannot form flagella by mutation in the hag gene and the bacteria are screened through the motility. Bacteria having mutation in the hag gene may be prepared according to the method of Kondoh et al. (Genetics 84, 403–421 (1976)). The strain W3623Hfla-am76 prepared by the above method may be used in this invention. In the case that foreign DNA is inserted into the hag gene in the vector, E. coli K-12 C600 r−m− hag::Tn10 or E. coli K-12 JA11 (deposited with Fermentation Research Institute Agency of Industrial Science and Technology as FERM P-8853 on Jul. 17, 1986 and transferred into the deposition under the Budapest Treaty as FERM BP-1233 on Dec. 4, 1986) that cannot form flagella by the reason that Kanamycin-resistant gene is introduced into the hag gene in its chromosome may be used. In the examples of this specification the strain K-12 C600 r−m− hag::Tn10 is employed. However, the strain K-12 JA11 deposited with the Fermentation Research Institute Agency of the Industrial Science and Technology can preferably be used in repeating this invention. As noted in the following examples, the vectors of this invention can be employed without difficulty by employing the strain K-12 JA11.

Since the strain transformed with the complete hag gene shows the motility, the DNA having the hag gene is prepared again from the strain showing motility. Namely, the DNA having the complete hag gene is prepared by fermenting the strain in a large scale and purifying it by usual centrifugation, removal of protein, ethanol precipitation and so on.

A DNA fragment having the hag gene is prepared by digesting the prepared DNA with suitable restriction enzymes and then inserted in an appropriate vector. Applicable restriction enzymes depend upon the DNA sequence carrying the hag gene. Such restriction enzymes are preferable as not digesting hag gene and cutting off unnecessary DNA sequence as much as possible. Suitable vectors are exemplified below; plasmid vector such as pN01523, pSC101, pRK353, pRK646, pRK248, pDF41, ColE1, pVH51, pAC105, RSF2124, pCR1, pMB9, pBR313, pBR322, pBR324, pBR325, pBR327, pBR328, pKY2289, pKY2700, pKN80, pKC7, pKB111, pKB158, pKH47, pHSV-106, pKK2333, pMK2004, pACYC1, pACYC184, pUC8, pUC9, pUC12, pUC13, pUC18, pUC19, pAT153, pUR222, pBT11, pJDB207, Homer 111, pHSV-106, ptac 12, ptrpL1, pSV-neo, cloDF13, R6K, F, RI, R6, Entp307, pC194, pE194, pA0501, pUB110, pT127 and so on, phage vector such as M13, λ gt. λ c, λ gt. λ B, λ WES λ C, λ WES. λ B, λ ZJvir. λ B', λ ALO. λ B, λ WES.T$_5$622 and so on, and vectors constructed from these vectors. Not restricted to only the above vectors, all vectors by which the hag gene can be carried and introduced into a host can be employed in this invention. A prepared vector carrying the hag gene may be minimized and the hag gene carried may be further transferred into other suitable vectors.

A prepared vector as noted above was purified according to the usual method and the whole sequence of the hag gene was determined. The sequencing can be performed by the usual methods such as the method of Maxam and Gilbert, the dideoxynucleotide chain termination method and so on. The whole base sequence of the hag gene is shown in FIG. 1. The amino acid sequence deduced from the base sequence is shown under the base sequence in FIG. 1.

Amino acid residues of N-terminal and C-terminal of protein flagellin of E. coli were analyzed and determined to be Ala-Gln-at N-terminal and -Gly at C-terminal, which are identical with the amino acid residues deduced from the base sequence. The experimental value of amino acid composition is very close to the value calculated from the base sequence.

In order to easily handle a prepared vector as an excretion vector, suitable linkers may be inserted into the hag gene of the prepared vector without destruction of the structure necessary for the excretion of flagellin by such an insertion. Said linkers may provide suitable restriction sites in the hag gene without a deficiency of the excretion function of flagellin, preferably providing a small number of restriction sites in the vector, more preferably providing a unique restriction site in the vector. For example, where the hag gene is inserted into pBR322, one or more linkers having a restriction site such as Hind$_{III}$, Avr$_{II}$, Bcl$_I$, BstE$_{II}$, Bgl$_{II}$, Hpa$_I$, Kpn$_I$, Sac$_I$, Sac$_{II}$, Sma$_I$, Sst$_I$, Sst$_{II}$, Xba$_I$, Xho$_I$ and Xma$_I$ are preferably inserted into the hag gene. Such an insertion of linkers makes it easy to insert a foreign gene into the hag gene.

Part of the hag gene that is produced by removing part unnecessary for excretion of the protein flagellin from the hag gene is utilized in an excretion vector. It was revealed that flagellin expressed by the hag gene is excreted even if amino acid residues at around the center of the flagellin are removed. Namely, where the vector which carries the hag gene lacking its center part is introduced into a bacteria not capable of forming flagella, the bacteria is transformed and forms flagella and shows motility. Moreover, where some linkers are inserted into around the center of the hag gene carried on a vector and exogenous DNA is inserted into the linker, the vector causes a host excrete exogenous protein fused with flagellin and form flagella.

Since the center of the hag gene codes for peptide concerning the antigencity of flagellin, the deficiency of the center portion of the hag gene is confirmed through the change of the antigencity of flagella. In this invention vectors carried by E. coli wherein the antigencity of flagella is changed, that is, that shows motility on a medium containing anti-flagella antibody, are prepared by cutting vectors carrying the hag gene at random, digesting them from the cut site, linking them with adding linkers for recyclization and introducing them into E. coli. The vectors can make E. coli form flagella and the linkers are inserted into the hag gene on the vectors. Since the DNA is cut and digested at random in this step, several kinds of vectors that have similar property but a little different sequence are prepared. The ordinary skilled person in this field can easily predict that such vectors will be prepared as different from the vectors prepared in this invention in the lacking portion of the hag gene in terms of the cut site and the number of bases digested from the cut site. Accordingly, this invention is not restricted into several vectors disclosed in this specification but includes vectors having above properties as well as vectors prepared in the step as noted above. This invention reveals that such a vector as lacking from 583rd to 1,143th bases (561 base pairs) of the hag gene and having 18mer linker in the lacking portion shows the above-mentioned properties.

If it is not necessary to make a host form flagella and only necessary to excrete a fused protein, the lacking portion of the hag gene on the vector may be expanded.

Moreover, to add the pHD1 mutation (see Example ⑩) to the vectors of this invention is efficient in making E. coli form a large number of flagella.

The abbreviations used in this specification are shown below.
DNA: deoxyribonucleic acid
cDNA: complementary DNA
ccDNA: closed circular DNA
RNA: ribonucleic acid
mRNA: messenger RNA
A: adenine
T: thymine
G: guanine
C: cytosine
ATP: adenosine triphosphate
TTP: thymidine triphosphate
GTP: guanosine triphosphate
CTP: cytidine triphosphate
dATP: deoxyadenosine triphosphate
dTTP: deoxythymidine triphosphate
dGTP: deoxyguanosine triphosphate
dCTP: deoxycytidine triphosphate
ddATP: dideoxyadenosine triphosphate
ddTTP: dideoxythymidine triphosphate
ddGTP: dideoxyguanosine triphosphate
ddCTP: dideoxycytidine triphosphate
DTT: dithiothreitol
Ala or A: alanine
Arg or R: arginine
Asn or N: asparagine
Asp or D: asparatic acid
Cys or C: cysteine
Gln or Q: glutamine
Glu or E: glutamic acid
Gly or G: glycine
His or H: histidine
Ile or I: isoluecine
Leu or L: leucine
Lys or K: lysine
Met or M: methionine
Phe or F: phenylalanine
Pro or P: proline
Ser or S: serine
Thr or T: threonine
Trp or W: tryptophan
Tyr or Y: tyrosine
Val or V: valine

EXAMPLE

① Recloning of the Hag Gene in pBR322

(A) Preparation of DNA of phageλ pfla-H2 having hag gene (a) Identification of phageλ pfla-H2

E. coli K-12 W3623Hfla-am76 (deposited with Fermentation Research Institute Agency of Industrial Science and Technology as FERM P-8619 on Jan. 25, 1986 and transferred into the deposition under the Budapest Treaty as FERM BP-1231 on Dec. 4, 1986; Genetics 84, 403-421 (1976)), which has mutation in hag gene and forms no flagellum as a result, is incubated overnight at 37° C. with shaking in trypton broth for phage λ (comprising 1% bactotrypton (DIFCO), 0.25% sodium chloride and 0.0005% thiamine hydrochloride, pH 7.0 before sterilization). To the incubated broth (0.1 ml) is added 0.1 ml of trypton broth containing several hundreds of phageλ pfla-H2 carrying the hag gene of E. coli K-12 KH552 (J. Bacteriol, 130, 736-745 (1977)) and then added 3.0 ml of trypton broth supplemented 0.6% agar at 47° C. and the resultant is put upon trypton plate supplemented 1.2% agar. After overnight incubation at 37° C., several hundred of plaques are formed.

Each plaque is transferred by a sterilized toothpick to a medium for the motility test (above-mentioned trypton broth supplemented 0.3% agar), and incubated at 37° C. for 7-8 hr. The bacteria infected by the phage capable of completely transforming the hag gene form colonies of motile area of 3-4 cm in diameter. The media having the plaques forming such a colony are turned upside down and to the lids are dropped a few drops of chloroform and allowed to stand at 37° C. for 10 min for sterilization.

(b) Incubation of phageλ pfla-H2

Said phageλ pfla-H2 is suspended in 0.1 ml of the trypton broth as noted above, using a sterilized toothpick. To this suspension is added 0.1 ml of E. coli K-12 C600 incubated overnight in trypton containing broth and then added 3 ml of trypton broth (46° C.) supplemented 0.6% agar. The resultant is put over trypton broth supplemented 1.2% agar and incubated at 37° C. for 5-6 in hr. After the strain C600 is almost lysed by phageλ pfla-H2, 5 ml of trypton broth is added thereto and incubated for 20-30 min. After a few drops of chloroform are added thereto, 0.6% agar put over is broken, transferred into a centrifuge tube together with 5 ml of the broth added later and centrifuged at 3,000 r.p.m. for 10 min to give a supernatant. The supernatant, to which are added a few drops of chloroform, is incubated at 37° C. for 5 min for sterilization to give a seed phage solution of phage λ pfla-H2. The seed phage solution is diluted $10^6$–$10^7$ times with trypton broth, 0.05 ml of which is mixed with 0.1 ml of C600 incubated overnight in trypton broth. To the resultant is added 3 ml of trypton broth (46° C.) supplemented 0.6% agar and put over trypton both supplemented 1.2% agar. The number of phage per 1 ml is calculated from the number of plaque emerged after overnight incubation at 37° C. The above-mentioned dilute seed phage solution (0.1 ml) containing $2 \times 10^7$ phages is mixed with 0.1 ml of the culture of C600 incubated overnight in trypton broth supplemented 0.2% maltose and allowed to stand at 37° C. for 10 min. Typton broth (46° C.) supplemented 0.6% agar (3 ml) is added thereto and put over trypton plate containing 1.2% agar. Fifty plates as noted above are prepared. The plates are incubated at 37° C. for 5–6 hr. After most of the strain C600 are lysed by phageλ pfla-H2, 5 ml of trypton broth is added to each plate, followed by further incubation for 20–30 min. A few drops of chloroform are added thereto and then 0.6% agar put over is broken, which is transferred into a centrifuge tube together with 5 ml of trypton broth and centrifuged at 3,000 r.p.m. for 10 min. The supernatant is recovered to give about 350 ml of the culture solution of the phage.

(c) Purifcation of phage λpfla-H2

The above-mentioned phage culture solution is ultracentrifuged at 25,000 r.p.m. at 4° C. for 90 min. (Beckman L8-55) ultracentrifuge, #30 rotor). After the supernatant is removed, a small quantity of TM buffer solution (10 mM Tris-HCl (pH8.0), 10 mM magnesium sulfate) is added to the precipitate. To this suspension is added 1.7 ml of TM buffer solution saturated with cesium chloride at 4° C. per 1.3 ml of the suspension, followed by centrifugation at 23,000 r.p.m. at 15° C. for 40 hr (Beckman L8-55, SW41 rotor). The phage gathering around the center of the centrifuge tube forms visible band. The portion of the band (c.a. 1 ml) is drawn out of the centrifuge tube with an injector and dialyzed overnight at 4° C. against TM buffer solution (10 mM Tris-HCl (pH 8.0), 1 mM $Na_2EDTA$).

(d) Preparation of DNA of λpfla-H2

To one part of the above suspension of phage λpfla-H2 are added 0.1 parts of 10×SSC buffer solution (1.5M sodium chloride and 0.15M sodium citrate), 0.02 parts of 0.5M $Na_2EDTA$ and 0.01 parts of 20% sodium dodecyl sulfate (SDS) and which is allowed to stand at 37° C. for 10 min. Same volume of TE buffer solution saturated with phenol is added thereto and applied to phenol extraction of DNA with a rotary extractor at 60 r.p.m. for 30 min. The content is transferred into a centrifuge tube and centrifuged at 8,000 r.p.m. at 20° C. with a high speed refrigerated centrifuge. The supernatant is transferred into a dialysis tube and dialyzed overnight against TE buffer solution. The dialysate is transferred into SW41 polymer centrifuge tube (Beckman) and 0.1 volumes of 3M sodium acetate and then 2 volumes of cold ethanol are added thereto, followed by allowing to stand overnight at −20° C. The resultant is centrifuged at 300,000 r.p.m. at 4° C. for 60 min with centrifuge (Beckman) to recover the precipitate. The precipitate is dissolved in 400 μl of TE buffer solution and determined to be about 300 μg of the purified DNA of λpfla-H2 from an absorbance at 260 nm.

(B) Presumption of the position of the hag gene on λpfla-H2 DNA (a) Digestion of λpfla-H2 DNA with EcoRI λpfla-H2 DNA is digested with EcoRI. To a reaction mixture (20 μl) containing 500 ng of λpfla-H2 DNA, 50 mM Tris-HCl (pH7.5), 7 mM $MgCl_2$, 100 mM NaCl, 7 mM 2-mercaptoethanol and 0.01% bovine serum albumin, which is heated to 37° C., is added 5 units/1 μl of EcoRI (Takara Shuzo Co., Ltd.), followed by allowing to react at 37° C. for 30 min. A solution (2 μl) for inhibiting enzyme reaction (a mixture of 50% glycerol, 1% SDS and 0.02% bromophenol blue) is added thereto so as to inhibit the reaction. The reaction mixture (5 μl) is charged a 0.8% agarose slabgel electrophresis. Using submarine agarose electrophoresis system (Marysol Industry Co., Ltd.) and a electrophoresis buffer solution containing 40 mM Tris-HCl (ph8.1), 5 mM sodium acetate and 1 mM $Na_2EDTA$, the electrophoresis is performed at constant voltage (80 V) for 30–60 min. After the electrophoresis the gel is soaked in the above buffer solution supplemented 0.5 μg/ml of ethidium bromide for c.a. 10 min and lightened with an ultraviolet lamp (280 nμ) to detect DNA band. As a result, it is determined that λpfla-H2 DNA is digested with EcoRI into 21.3, 17.0, 5.82 and 3.54 kb fragments. Where DNA of bacteriophage λCI857S7 (Takara Shuzo Co., Ltd.) is digested with EcoRI in the same manner, fragments of 21.3, 5.82 and 3.54 kb are detected but fragment of 17.0 kb is not done. Accordingly, it is deduced that the fragment of 17.0 kb contains DNA fragment containing hag gene of E. coli.

(b) Digestion of λpfla-H2 DNA with SalI

To a mixture containing 10 mM Tris-HCl (pH7.5), 7 mM $MgCl_2$, 175 mM NaCl, 0.02 mM EDTA, 7 mM 2-mercaptoethanol and 0.01% bovine serum albumin is added 500 ng of λpfla-H2 DNA, digested with $Sal_I$ in the same manner as noted above and applied to an agarose gel electrophoresis. The λpfla-H2 DNA is digested into 32.7 and 15.3 kb fragments by $Sal_I$. Since a fragment of 15.3 kb is generated also in a digestion of λCI857S7 DNA with $Sal_I$, it is deduced that the fragment of 32.7 kb carries a DNA fragment containing the hag gene.

FIG. 2 shows a result of a digestion of λpfla-H2 with EcoRI (①-B-a) and $Sal_I$ (①-B-b) and a deduced position of a DNA fragment derived from chromosome carrying the hag gene of E. coli.

(Cloning in vector pBR322

λpfla-H2 DNA (2.5 μg) is digested with EcoRI in 100 μl of a reaction mixture according to ①-B-a. After inhibiting the reaction by heating the mixture to 70° C. for 5 min, 10 μl of 3M sodium acetate and 220 μl of cold ethanol are added thereto, followed by allowing to stand overnight at −20° C. After 10 min centrifugation (Microfuge, Beckman) the supernatant is removed and the precipitate is dissolved in 70 μl of TE buffer solution.

To the resultant (λpfla-H2 DNA digested with EcoRI) are added a reaction mixture and $Sal_I$ (total volume 100 μl) for digestion in a similar manner to ①-B-b. After the reaction, ethanol precipitation is performed in the same way as noted above and the precipitate is dissolved in 50 μl of TE buffer solution.

Besides, to a reaction mixture (144 μl) prepared in a similar manner to ①-B-a, which contains 2 μg of pBR322 cc-DNA (Takara Shuzo Co., Ltd.), are added 24 units/4 μl of EcoRI and 16 units per 2 μl of $Hind_{III}$ and allowed to react at 37° C. for 30 min. After inhibiting the reaction by heating the mixture to 70° C. for 5 min, ethanol precipitation is performed and the precipitate is dissolved in 100 μl of TE buffer solution. Then, the resultant is digested with $Sal_I$, followed by ethanol precipitation. The precipitate is dissolved in 40 μl of TE buffer solution.

To 98 μl of T4 DNA ligase reaction mixture (66 mM Tris-HCl (pH7.6), 6.6 mM $MgCl_2$, 10 mM DTT and 1 mM ATP) containing 2.5 μg of λpfla-H2 DNA digested with EcoRI and $Sal_I$ and 250 μg of pBR322 digested with EcoRI, $Sal_I$ and $Hind_{III}$ is added 0.2 units/2 μl of T4 DNA ligase (Takara Shuzo Co., Ltd., Lot 301) and allowed to react at 22°–23° C. for 6 hr. After ethanol precipitation the precipitate is dissolved in 20 μl of TE buffer solution.

Competent W3623H fla-am76 strain (210 μl) is mixed with 250 ng/20 μl of the above DNA for infection. The mixture is inoculated into LB broth (pH 7.0-7.2) containing 1% Bacto-Trypton (Difco), 0.5% yeast extract and 0.5% NaCl and incubated at 37° C. for 1 hr with shaking. On LB plate containing 0.005% ampicillin and 1.5% agar is spread 0.1 ml of the resultant. After overnight incubation at 37° C., ampicillin-resistant strain growing up is inoculated into a medium for the motility test containing 0.005% ampicillin. Four of 180 colonies tested form motile area. One of these 4 colonies is purified twice in LB agar medium containing 50 μg/ml of ampicillin to establish strain W3623Hfla-am76 (pBR322/hag9), which has been deposited as FERM P-8620 with the Fermentation Research Institute Agency of the Industrial Science & Technology since Jan. 25, 1986 and transferred into the deposition under the Budapest Trreaty as FERM BP-1232 since Dec. 4, 1986.

(D) Investigation of structure of recombinant plasmid pBR322/hag9

(a) Purification of pBR322/hag9 cc-DNA

Strain W3623Hfla-am76 (pBR322/hag9) is inoculated in 5 ml of LB broth containing 50 μg/ml of ampicillin and incubated overnight at 37° C. with shaking. This overnight culture is transplanted in 1L of LB broth containing 50 μg/ml of ampicillin, incubated overnight at 37° C. with shaking and centrifuged at 5,000 r.p.m. at 4° C. for 10 min to recover the bacteria.

The recovered microorganisms are suspended in 20 ml of solution I (50 mM glucose, 25 mM Tris-HCl (pH 8.0) and 10 mM EDTA), in which 100 mg (powder) of lysozyme (Sigma) is dissolved. The mixture is allowed to stand at room temperature for 10 min with occasionally stirring and 40 ml of Solution II (0.2N sodium hydroxide and 1% sodium dodecyl sulfate) is gradually mixed therewith, followed by allowing to stand in ice for 10 min. Then, the mixture, to which 30 ml of ice-cooled 5M potassium acetate (pH 4.8) is added, is allowed to stand in ice for 10 min. After centrifugation at 10,000 r.p.m. at 4° C. for 30 min, the supernatant is recovered in 100 ml-measuring cylinder to measure the volume and transferred to a centrifuge tube, with which 0.6 parts of isopropanol is mixed, followed by allowing to stand at room temperature for 15 min. After centrifuging at 10,000 r.p.m. at 15° C. for 30 min and removing the supernatant, 140 ml of 70% ethanol is added to the precipitate. After centrifuging the resulting solution at 10,000 r.p.m. at 4° C. for 30 min and removing the supernatant, the precipitate is almost dried in a vacuum desiccator and dissolved in TE buffer solution. The solution is transferred into 50 ml-measuring cylinder to adjust the volume to 30 ml, in which 0.3 ml of 10% sodium dodecyl sarcosinate, 2 ml of 10 mg/ml ethidium bromide and then 33.915 g of cesium chloride are dissolved. After centrifuging at 36,000 r.p.m. at 15° C. for 40 hr (L8-55 ultracentrifuge, VTi 50 rotor, Beckman), 2 fluoresent bands are observed under an ultraviolet lamp. The under band is drawn from the side of the centrifuge tube with a syringe. Then the content of the syringe is applied to ultracentrifugation at 36,000 r.p.m. at 15° C. for 20 hr (Beckman L8-55 ultracentrifuge, VTi 65 rotor). In the same way as mentioned above an under band which shows fluoresence under an ultraviolet lamp is drawn with a syringe and transferred to a test tube. Ethidium bromide is removed by extracting 3 times with isopropanol saturated with cesium chloride. The water phase is dialyzed overnight against TE buffer solution.

The dialyzed sample is put in a tube for SW 50.1 rotor (Beckman), with which 0.1 parts of 3M sodium acetate and 2 parts of ethanol are mixed, followed by allowing to stand overnight at −20° C. (ethanol precipitation).

After centrifuging the rsulting solution at 30,000 r.p.m. at 4° C. for 30 min (Beckman L8-55 ultracentrifuge) and removing the supernatant, the precipitate is slightly dried in a vacuum desiccator, dissolved in 0.6 ml of TE buffer solution and allowed to stand overnight at 4° C. RNase (Sigma) heated to 96° C. for 10 min is added thereto in a way to bring a final concentration of 10 μg/ml and allowed to stand at room temperature for an hour.

In a tube for SW 50.1 rotor is poured 4 ml of 1M sodium chloride-TE buffer solution. The above sample is put over it and centrifuged at 40,000 r.p.m. for 6 hr. The supernatant is removed and the precipitate is dissolved in 0.2 ml of TE buffer solution. An aliquot is diluted and the DNA concentration is calculated from the absorbance at 260 mμ.

(b) Digestion of pBR322/hag9 cc-DNA with EcoRI and Sal$_I$

Figure 3:
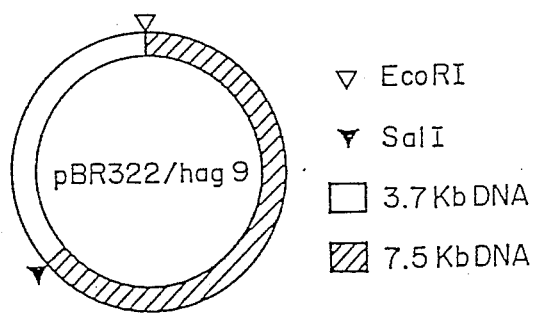
FIG. 3 shows a result of digestion of pBR322/hag9 with EcoRI and Sal$_I$.

In a similar way to ①-B-a and ①-B-b, pBR322/hag9 cc-DNA is digested with EcoRI and Sal$_I$ and applied to agarose gel electrophoresis to observe that the cc-DNA alters to linear DNA, which means that the cc-DNA has an unique restriction site of EcoRI and Sal$_I$. With EcoRI is digested pBR322/hag9 DNA and the reaction is inhibited by heating to 70° C. Successively, the resultant is digested with Sal$_I$ and the raction is inhibited by heating to 70° C. The resultant is applied to agarose gel electrophoresis to observe about 7.5 kb and about 3.7 kb fragments (λCl857S7 DNA digested with Hind$_{III}$ is used as DNA size marker). The about 7.5 kb and about 3.7 kb fragments are derived from λpfla-H2 DNA and pBR322, respectively (see FIG. 3). (c) Digestion of pBR322/hag9 cc-DNA with BamHI To 10 μl of a reaction mixture containing 10 mM Tris-HCl (pH8.0), 7 mM magnesium chloride, 100 mM sodium chloride, 2 mM 2-mercaptoethanol, 0.01% bovine serum albumin and 1 μg of pBR322/hag9 cc-DNA is added 10 units/μl of BamHI and the reaction is performed in a similar way to digestion with EcoRI in ①-B-a. The resultant is applied to agarose gel electrophoresis. λCl857S7 DNA digested with Hind$_{III}$ is used as DNA size marker. As a result, pBR322/hag9 cc-DNA is digested with BamHI into about 5.7, 3.5 and 1.85 kb fragments.

Then, BamHI restriction site on pBR322/hag9 is determined by the following manner; pBR322/hag9 DNA completely digested with EcoRI is incompletely digested with BamHI and pBR322/hag9 DNA completely digested with Sal$_I$ is incompletely digested with BamHI. Firstly, 1 μg of pBR322/hag9 cc-DNA is digested in a test tube with EcoRI or Sal$_I$ according to the method in ①-B-a and ①-B-b. The reaction is performed at 37° C. for an hour and inhibited by heating to 70° C. for 5 min.

Then, 1 unit/μl of BamHI is added to each test tube and 5 μl aliquots are drawn 2 min and 5 min later, to which a mixture for inhibiting the reaction containing 50% glycerol, 1% SDS and 0.02% bromophenol blue is added. To a remained reaction mixture (11 μl) is added 1 unit/μl of BamHI 9 min later and 5 μl aliquots are drawn 10 min and 20 min later, to which the mixture for inhibiting the reaction (0.5 μl) is added. Each sample is subjected to 0.8% agarose gel electrophoresis to determine size of produced fragments. λCl857S7 DNA digested with Hind$_{III}$ is used as DNA size marker. In a sample digested with EcoRI completely and with BamHI for 20 min are observed fragments A (5.4 kb), B (3.9 kb), C (1.95 kb) and D (0.73 kb). In a sample digested with EcoRI completely and with BamHI for 2 min or 5 min are observed fragments corresponding to fragments D, C, B, B+D, A, B+C, B+C+D, A+C, A+B+C and A+B+C+D according to size. In a sample digested with Sal$_I$ completely and with BamHI for 20 min are observed fragments a (4.7 kb), b (3.8 kb), c (1.95 kb) and d (1.26 kb). In a sample digested with Sal$_I$ completely and with BamHI for 2 min or 5 min are observed fragments corresponding to fragments d, c, c+d, b, a, b+c, b+c+d, a+b, a+b+c, a+b+c+d according to size. FIG. 4 shows BamHI restriction sites on pBR322/hag9.

(E) Construction of recombinant plasmid pBR322/hag93

To 56 μl of a reaction mixture containing 10 mM Tris-HCl (pH 8.0), 7 mM magnesium chloride, 100 mM sodium chloride, 2 mM 2 mercaptoethanol and 0.01% bovine serum albumin is added 10 μg of pBR322/hag9 cc-DNA in 30 μl of TE buffer solution and then added 40 units of BamHI (4 μl) and allowed to react at 37° C. for 2 hr. With the resultant is mixed 60 μl of phenol chloroform (1:1) and centrifuged with Microfuge to recover the supernatant. To this supernantant is again added 60 μl of phenol chloroform and centrifuged with Microfuge. With the supernatant is well mixed 60 μl of chloroform and which is centrifuged with Microfuge to recover the supernatant. Again, chloroform is added to the supernatant and centrifuged with Microfuge to recover the supernatant. To this supernatant are added 0.1 parts of 3M sodium acetate and 2 parts of ethanol and allowed to stand overnight at −20° C. After centrifugation with Microfuge, the precipitate is dissolved in 11 μl of TE buffer solution.

DNA linking reaction is achieved as follows. To 11 μl of the above sample solution are added 4 μl of 250 mM Tris-HCl (pH 7.6) containing 33 mM magnesium chloride, 2 μl of 100 mM ATP, 2 μl of 100 mM DTT and then 1 unit/ml of T4 DNA ligase (Takara Shuzo Co., Ltd., Code No. 2010B, Lot No. 301) and allowed to react at 13°-° C. for 6 hr.

Strain W3623Hfla$^-$-hag76 is transformed with 10 μl of the above reacted mixture to form 200 colonies on LB agar medium containing 50 μg/ml of ampicillin, which are transplanted in the medium for the motility test containing 50 μg/ml of ampicillin to give 14 strains showing motility. Plasmid DNA carried by the 14 strains is digested with BamHI according to what is called rapid plasmid DNA analysis*$^1$. A plasmid lacking B fragment of pBR322/hag9 (see FIG. 4) is found out and named pBR322/hag93 (see FIG. 5).
*1 Rapid Plasmid DNA Analysis A colony is transplanted in LB broth containing 50 μg/ml of ampicillin and incubated overnight at 37° C. In a eppendorf tube is transferred 1.5 ml aliquot and centrifuged with Microfuge for 1 min. The supernatant is removed as much as possible and the precipitate is suspended in 100 μl of solution $_I$ (50 mM glucose, 10 mM EDTA-Na$_2$, 25 mM Tris-HCl (pH 8.0) and 4 mg/ml lysozyme (Sigma)). After allowing to stand at room temperature for 5 min, 200 μl of solution$_{II}$ (0.2N sodium hydroxide and 1% SDS) is gradually added thereto and allowed to stand in ice (0° C.) for 5 min.

Then, 150 μl of ice-chilled 3M potassium acetate (adjusted to pH 4.8 with gracial acetic acid) is well mixed therewith. After allowing to stand at 0° C. for 5 min, the resulting mixture is centrifuged at 4° C. with Microfuge and the supernatant is transferred into another eppendorf tube. Same volume of phenol chloroform (1:1) is mixed therewith and the mixture is centrifuged with Microfuge for 2 min. The resulting supernatant is transferred into another eppendorf tube. After mixed with 2 parts of ethanol, it is allowed to stand at room temperature for 2 min. After the centrifugation for 5 min with Microfuge and removing the supernatant, a solution remained on the inner wall of the tube is removed with paper as much as possible. To the tube is added 1 ml of 70% ethanol, mixed well and centrifuged with Microfuge for 5 min. The supernatant is completely removed and the precipitate is dried in a vacuum desiccator and dissolved in 50 μl of TE buffer solution containing 20 μg/ml of RNase (heated to 95° C. for 10 min, Sigma). Into another tube is transferred 10 μl aliquot, to which 1.2 μl of 10×BamHI reaction mixture (100 mM Tris-HCl (pH 8.0), 70 mM magnesium chloride, 1000 mM sodium chloride, 20 mM 2-mercaptoethanol and 0.1% bovine serum albumin) is added. One unit of BamHI is added thereto and the reaction is performed at 37° C. for 1 hr. After the reaction, 0.8 μl of the mixture is applied to agarose gel electrophoresis.

(F) Investigation of Structure of pBR322/hag93

(a) Purification of pBR322/hag93 DNA

From strain W3623Hfla-am76 (pBR322/hag93) is purified pBR322/hag93 cc-DNA in a similar manner to ①-D-a.

(b) Digestion of pBR322/hag93 cc-DNA with Hinc$_{II}$

Figure 6:
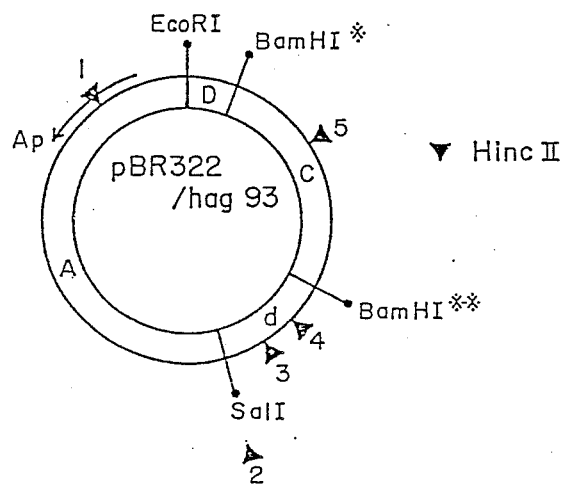
FIG. 6 shows 5 Hinc$_{II}$ restriction sites on pBR322/hag93.

To 50 μl of a mixture containing 10 mM Tris-HCl (pH 8.0), 7 mM magnesium chloride, 60 mM sodium chloride, 7 mM 2-mercaptoethanol and 1 μg of pBR322/hag93 is added 3 units of Hinc$_{II}$ (0.5 μl) and allowed to react at 37° C. for 30 min. The size of the fragments digested by Hinc$_{II}$ is measured by agarose gel electrophoresis in a similar way to ①-B-a. As a result, fragments of 3.4, 1.85, 1.68, 0.53 and 0.41 kb are observed. Thus, 5 restriction sites of Hinc$_{II}$ on pBR322/hag93 are estimated as shown in FIG. 6.

(c) Subcloning of Hinc$_{II}$ fragment of 1.68 kb into pUC9

It is deduced that the hag gene exists in the fragment of 1.68 kb (①-F-b) between Hinc$_{II}$ restriction sites (5) and (4). This 1.68 kb fragment is subcloned in Hinc$_{II}$ site on plasmid vector pUC9.

In a similar manner to ①-B-a, pBR322/hag93 cc-DNA is digested with EcoRI; 30.5 μl of a mixture containing 10 μg of pBR322/hag93 cc-DNA and 18 units of EcoRI is allowed to react at 37° C. for 1.5 hr. To 29.5 μl of the mixture is added 5 μl of 1M Tri-HCl (pH 8.0) and 63 μl of water. Further, 0.236 units/2 μl of alkaline phosphatase of E. coli (BAP, Takara Shuzo Co., Ltd., Lot 1112) is added thereto and allowed to react at 65° C. for 30 min. The mixture is extracted twice with same volume of phenol chloroform (1:1) and then twice with same volume of chloroform following Ethanol precipitation. The precipitate is dissolved in 20 μl of TE buffer solution. To 20 μl of the mixture (10 μg DNA) is added 20 units/4 μl of Hinc$_{II}$. After adjusting the total volume to 40 μl, the reaction is performed at 37° C. for 2 hr in a similar way to ①-F-b. The reaction is inhibited by heating to 65° C. for 10 min. Ethanol precipitation is performed and the precipitate is dissolved in 20 μl of TE buffer solution.

Besides, in a similar way to ①-B-a 5 μg of plasmid vector pUC9 (Pharmacia) is digested in 30 μl of a reaction mixture containing 15 units of Hinc$_{II}$. The reaction is performed at 37° C. for 1.5 hr and then inhibited by heating to 60° C. for 10 min. Ethanol precipitation is achieved and the precipitate is dissolved in 6 μl of TE buffer solution.

Figure 7:
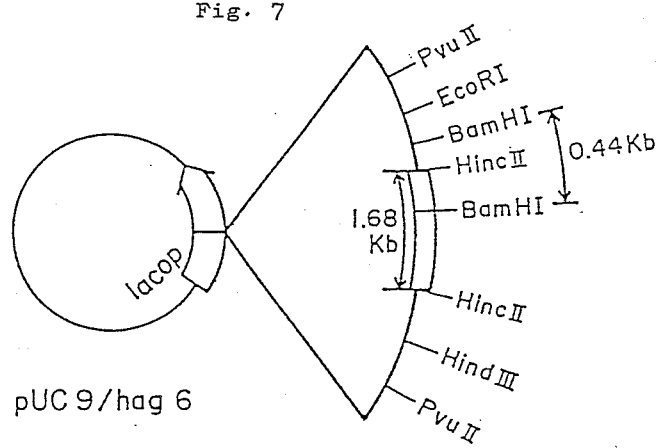
FIG. 7 shows pUC9/hag6.

DNA linking reaction is performed in a reaction mixture containing 5 μg/5 μl of pBR322/hag9 digested with EcoRI, BAP and Hinc$_{II}$, 5 μg/6 μl of plasmid vector pUC9 digested with Hinc$_{II}$ and 0.1 units/1 μl of T4 DNA ligase according to ①-C. With the resultant is transformed strain W3623fla-am76. Colonies formed on LB medium containing 50 μg/ml of ampicillin is inoculated into the medium for the motility test containing 50 μg/ml of ampicillin. Twelve colonies of 1,112 colonies formed shows motility. Two strains thereof is applied to the rapid plasmid DNA analysis. A recombinant plasmid, which is digested to form 1.68 kb fragment with Hinc II and 0.44 and 4.0 kb fragments with BamHI, is named pUC9/hag6 (see FIG. 7).

Recombinant plasmid pBR322/hag93 has Hinc II fragment of 1.68 kb shown in ①-F-b. The Hinc II fragment gives strain W3623Hfla-am76 motility when the fragment is inserted in plasmid vector pUC9 in right direction (from Hinc II (5) to BamHI in the fragment) along direction of transcription of lac promoter. Thus, the 1.68 kb fragment completely contains a structural gene of the hag gene in direction of from Hinc II (5) to BamHI.

(d) Subcloning of Hind III-BamHI fragment of recombinant plasmid pUC9/hag6 in plasmid vector pUC8

From strain W3623Hfla-am76 (pUC9/hag6) is purified pUC9/hag6 cc-DNA in a similar manner to ①-D-a.

In 160 μl of a reaction mixture containing 36 units/6 μl of EcoRI, 36 units/3 μl of Hind III, 30 units/6 μl of Pvu II and 15 μg/5.1 μl of pUC9/hag6 cc-DNA is digested pUC9/hag6 cc-DNA with EcoRI, Hind III and Pvu II at 37° C. for 2 hr. Besides, in 60 μl of a reaction mixture containing 18 units/3 μl of EcoRI, 18 units/1.5 μl of Hind III and 5 μg/20 μl of pUC8 (Pharmacia) is digested pUC8 with EcoRI and Hind III at 37° C. for 2 hr according to ①-B-a.

In the above both reactions ethanol precipitation is performed by extracting twice the phenol chloroform (1:1) and then twice with chloroform. In the reaction of pUC9/hag6 the precipitate is dissolved in 30 μl of TE buffer solution and in the reaction of pUC8, the precipitate is dissolved in 10 μl of TE buffer solution. Then, DNA linking reaction is performed in 21 μl of a reaction mixture containing 4 μg/8 μl of digested pUC9/hag6 2 μg/4 μl of digested pUC8 and 1 unit/1 μl of T4 DNA ligase according to ①-C. After the reaction, strain W3623Hfla-am76 is transformed therewith. Colonies formed on LB agar medium containing 50 μg/ml of ampicillin are investigated by the rapid plasmid analysis as to whether or not they have recombinant cc-DNA of 4.4 kb (2.7 kb (pUC8)+1.68 kb) to give 40 colonies having 4.4 kb cc-DNA. The motility of these 40 colonies is investigated on the medium for the motility test containing 50 μg/ml of ampicillin. As a result, none of these 40 colonies shows motility. This means that the hag gene is not expressed when the 1.68 kb fragment is inserted in a downstream of lac promoter of pUC8 in reverse direction to that of the lac promoter.

Thus, the 1.68 kb fragment includes the protein coding region of the hag gene (①-F-c) but not its complete promoter region.

A recombinant plasmid carried by one of the above 40 colonies is named pUC8/hag6 and purified in accordance with ①-D-a.

② Sequencing of the hag gene (A) Sequencing of the hag gene

As it is revealed that the protein coding region of the hag gene is involved in the Hinc II fragment of 1.68 kb (①-F-c and ①-F-d), this fragment is sequenced.

The sequencing of the 1.68 kb fragment is achieved by the ordinaly dideoxynucleotide chain termination method employing M13 phage vector. Certain fragments (identified by arrows in FIG. 8) produced by digesting cc-DNA of pBR322/hag93, pUC9/hag6 and pUC8/hag6 with Hap II, Hinc II, Taq I, Sau3A, BamHI and Pst I (Takara Shuzo Co., Ltd.) are cloned in M13 mp8, mp9 and mp18.

The pUC8/hag6 or pUC9/hag6 DNA is denaturated in a solution containing 0.1M sodium hydroxide and 0.1 mM EDTA-Na$_2$ to provide single strand DNA, which is applied to the dihydroxynucleotide dihydroxynucleotide chain termination method for sequencing of the 1.68 kb fragment.

Figure 8:
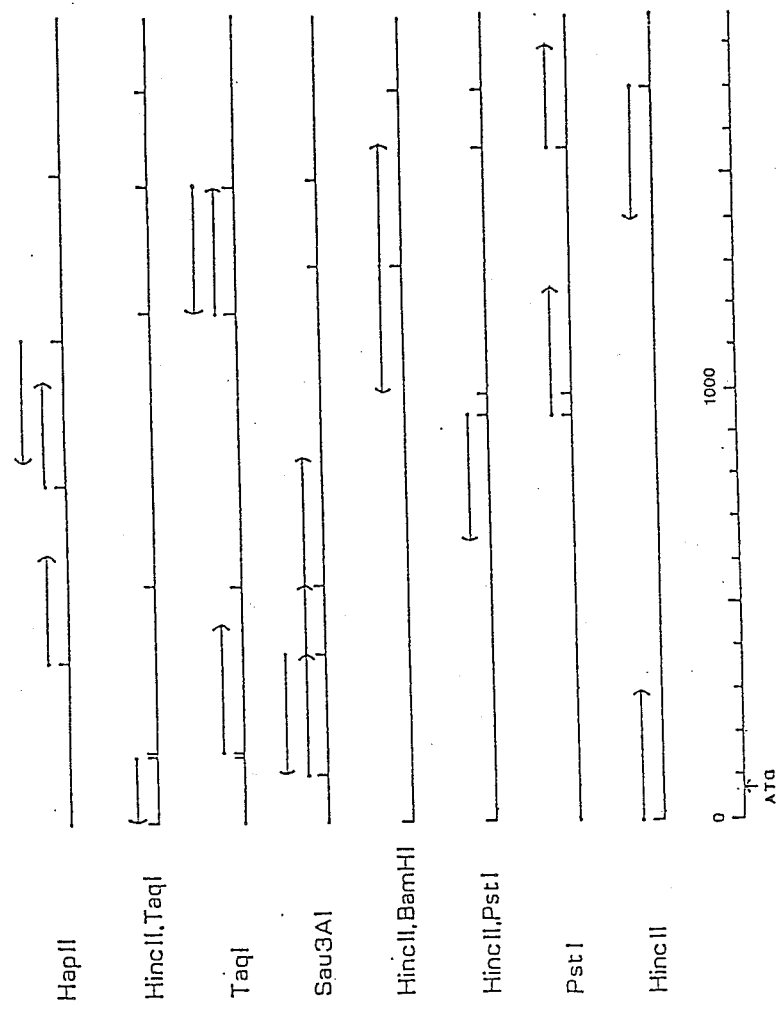
FIG. 8 shows a schedule for sequencing of hag gene.

FIG. 8 shows the scheme for sequencing. The lines in the figure are shown in direction of 5' to 3'.

FIG. 9 shows whole primary structure of the hag gene determined in the above sequencing. The DNA sequence from initiation codon ATG to its downstream 60th base of the hag gene is identical with the known DNA sequence (J. Bacteriol. 155, 78 (1983)).

(B) Determination of amino acid residues at amino and carboxy termini of protein flagellin (a) Purification of flagellin E. coli K-12 W3110 is purified in LB agar medium and incubated overnight at 37° C. for colonization. A suitable colony is inoculated into the medium for the motility test by pricking and incubated at 37° C. for 4-5 hr. The strain lying around the periphery of the motile zone is transplanted in 100 ml of LB broth and incubated overnight at 37° C. The culture (3-4 ml/plate) is spread on LB agar medium in a plate (80×225 mm, Eiken) and incubated overnight at 37° C. On the surface of the culture is poured a small amount of buffer solution P (0.15M sodium chloride and 10 mM potassium dihydrogenphosphate-disodium hydrogenphosphate, pH 6.8). The resulting culture is collected with a spreader (Nissui) and suspended in buffer solution P.

From 90 plates is prepared about 250 ml of the above suspension, which is transferred into 1-Erlenmeyer flask with cap, shaken hard 600 times and centrifuged at 8,000 r.p.m. at 4° C. for 15 min. The supernatant is filtered through glasswool. After centrifuging the filtrate at 25,000 r.p.m. at 4° C. for 1 hr (Beckman Ultracentrifuge, rotor #30), the precipitate is suspended in about 20 ml of buffer solution P. After centrifugation at 8,000 r.p.m. at 4° C. for 15 min, the supernatant, which contains flagellar, is recovered and heated to 65° C. for 5 min. After centrifugation at 25,000 r.p.m. at 4° C. for 90 min (Beckman Ultracentrifuge, rotor #30), the supernatant (14.5 ml) is recovered to give a crude flagellin fraction.

Then, the crude flagellin fraction is diluted 3 times with 10 mM potassium dihydrogenphosphate-disodium hydrogenphosphate solution (pH 6.8) containing 0.05M sodium chloride and applied to a DEAE-cellose column (DE52, Whatman Chemical Separation), which is washed with 98 ml of the above solution for dilution and eluted with 0.05–0.7M sodium chloride dissolved in 10 mM potassium dihydrogenphosphate-disodium hydrogenphosphate (pH 6.8) according to the density gradient technique. Flagellin is eluted (18.8 ml) when the concentration of sodium chloride is 0.3M. Employing bovine serum albumin as standard protein, the protein flagellin is measured by a protein assay kit (Bio-Rad) to be 26.17 mg/18.8 ml.

(b) Determination of amino acid residues at amino and carboxy termini and of amino acid composition Prior to analyzing, purified flagellin prepared in ②-B-a is centrifuged and concentrated by 6.5 mg/ml, which is dialyzed to give a starting sample for each analysis.

Determination of amino acid residues of amino terminus is achieved according to the Edman method. As a result the sequence of N terminal is determined to be Ala(1)-Gln(2)-, which is identical with Ala(1)-Gln(2)-deduced from the DNA sequence shown in FIG. 9.

Determination of amino acid residue of carboxy terminus is performed in accordance with the usual method using carboxypeptidase P to be identified as Gly, which is identical with Gly(497) deduced from the DNA sequence shown in FIG. 9.

For the analysis of amino acid composition, firstly the purified flagellin (6.5 mg/ml) is dissolved in 0.1% ammonia water. To 10 μl of the resulting mixture is added 50 μl of 4M methansulfonic acid containing 0.2% indolethylamine, which is hydrolysed at 110° C. for 24 hr. To the resultant are added 47 μl of 4N sodium hydroxide and 403 μl of 0.2N sodium citrate to prepare a sample for the analysis. The analysis is achieved with Hitachi amino acid analyzer model 835. Table 1 shows a comparison of the found amino acid composition with that deduced from the DNA sequence.

TABLE 1

| Amino Acid Composition of Flagellin of E. coli K—12 | | |
|---|---|---|
| Amino acid | Found(a) | Calcd. |
| Ala | 58.1 | 59 |
| Val | 32.8 | 33 |
| Leu | 37.5 | 37 |
| Ile | 27.0 | 28 |
| Gly | 45.3 | 44 |
| Pro | 6.0 | 6 |
| Cys | 0.0 | 0 |
| Met | 2.7 | 3 |
| His | 0.0 | 0 |
| Phe | 5.0 | 5 |
| Tyr | 9.9 | 10 |
| Trp | 0.0 | 0 |
| Asn(+Asp) | (88.7) | 48(87) |
| Gln(+Glu) | (41.5) | 27(41) |
| Ser | 42.8(b) | 43 |
| Thr | 63.3(b) | 65 |
| Lys | 25.4 | 25 |
| Arg | 10.2 | 11 |

(a)Calculated by regarding Phe residue as 5.0.
(b)Revised by taking hydrolysis into consideration.

③ In vitro preparation of hag gene variant in H antigenicity (A) Digestion of pBR322/hag93 ccDNA with deoxyribonuclease I (DNase I)

To ethanol precipitation is subjected pBR322/hag93 ccDNA (1.35 mg, 1 ml) in TE buffer solution and dissolved in 50 ml Tris-HCl (pH7.3). A reaction mixture (340 μl) containing 125 μg of the DNA, 6 ng of DNase I (Takara Shuzo Co., Ltd.) and 1 mM manganese chloride in 50 mM Tris-HCl (pH7.3) is allowed to react at 37° C. for 10 min and immediately same volume of phenol-chloroform (1:1) is added thereto for inhibiting the reaction. The resultant is applied to phenol-chloroform extraction in the way similar to ①-E. After ethanol precipitation, the precipitation is dissolved in 200 μl of TE buffer solution.

The solution is developed by agarose gel electrophoresis and DNA is extracted from the gel piece of the fluorescent band corresponding to linear monomer (as size marker of linear monomer pBR322/hag93 DNA digested with EcoRI is employed). The extract is subjected to ethanol precipitation to give about 2 μg of linear pBR322/hag93 DNA.

(B) Digestion with exonuclease Bal31

The DNA in ③-A is dissolved in 14 μl of water and distributed into 7 fractions. Then, to 2μ of aliquots, 2 μl of Bal31 reaction mixture (24 mM calcium chloride, 24 mM magnesium chloride, 200 mM sodium chloride, 40 mM Tris-HCl (pH8.0) and 2 mM EDTA-2Na) is added thereto and incubated at 30° C. for 3 min.

Bal31 enzyme solution (Takara Shuzo Co., Ltd.) is diluted in a solution comprising 12 mM calcium chloride, 12 mM magnesium chloride, 100 mM sodium chloride, 20 mM Tris-HCl (pH8.0), 1 mM EDTA-2Na and 0.1% bovine serum albumin to 6.02, 3.01, 1.51, 0.76, 0.38, 0.19, 0.10 unites/ml. To the above DNA mixture is added 4 μl of the Bal31 mixture of each concentration and allowed to react at 30° C. for 10 min. Then, 1μ of ethylene glycol bis(β-aminoethyl ether)-N,N,N',N'-tetraacetic acid (EGTA) is added thereto and ice-chilled. The contents of the 7 reaction tubes are put together and applied to phenol chloroform extraction and ethanol precipitation in a way similar to ①-E.

(C) Repair with E. coli DNA polymerase I large fragment (klenow fragment) and ligation in the presence of Hind III linker The DNA of ③-B is dissolved in 3 μl of TE buffer solution. This 3 μl of the DNA (about 2 μg) is allowed to react at 30° C. for 30 min with 1 μl of 10×nick translation buffer (0.5M Tris-HCl (pH7.2), 0.1M magnesium sulfate, 1 mM dithiothreitol and 500 μg/ml bovine serum albumin), 4 μl of dNTPs (1 mM dATP, 1 mM dTTP, 1 mM dGTP and 1 mM dCTP, Takara Shuzo Co., Ltd.), 1 μl of klenow fragment (3 units/μl, Takara Shuzo Co., Ltd.) and 1 μl of water. Then, a solution comprising 10 μl of the above reaction mixture, 4 μl of 5×ligation buffer (0.25M Tris-HCl (pH7.4), 0.05M magnesium chloride, 5 mM spermidine and 0.5 mg/ml bovine serum albumin), 1 μg/1 μl of Hind III linker (5'-CAAGCTTG, Takara Shuzo Co., Ltd.), 2 μl of 100 mM dithiothreitol, 2 μl of 10 mM ATP and 2 units/2 μl of T4DNA ligase is allowed to react at 16° C. for 16 hr.

(D) Transformation and selection of the strain variant in H-antigencity

E. coli K-12 C600 r−m− hag::Tn10 is transformed with the above resultant in ③-C. The strain C600r−m− hag::Tn10 is of r− (restriction minus) m− (modification minus) of a strain C600 (thr-1, leu-6, thi-1, supE44, lacY1, tonA21, λ−) and has an inactive hag gene in which Tn10 in inserted. About 8,600 colonies of transformants are formed on LB agar medium containing 50 μg/ml of ampicillin. About 5,000 colonies thereof are incubated at 37° C. for 5-6 hr on the medium for the motility test containing 1/10 volume of anti-flagella polymer antiserum. Twelve strains (group A) which show good motility as well as that on the medium for the motility test containing no antiserum are selected. Further, 4 strains (group B) which show apparent motility in incubation at 37° C. for 20 hr even in the presence of the antibody are selected.

An antigen used in preparing anti-flagella polymer antiserum is prepared by the method as follows. To 13.9 mg/10 ml of purified flagellin is added ammonium sulfate at a concentration of 60% (w/v) and the mixture is allowed to stand overnight at 4° C. and centrifuged at 15,000 g for 15 min. The precipitate is suspended in the buffer solution P (1.3 ml) and dialyzed against the buffer solution P. As an adjuvant an incomplete adjuvant (DIFCO) is employed. At first, 3 mg of the antigen is subcutaneously injected to each rabbit (New Zealand White) at both foot pads and the thigh. On days 9 and 14 the same treatments are performed. On day 21 the whole blood is drawn from the carotid artery. Thereafter a crude serum fraction is prepared by the usual method.

(E) Analysis of the hag gene of the strain variant in H-antigencity (a) Rapid plasmid DNA analysis Whether the plasmids carried by the groups A and B selected in ③-D are digested with Hind III or not is analysed by the rapid plasmid DNA analysis method.

The plasmids of 4 strains from the group A and 1 strain from the group B are digested with Hind III. Since these plasmids are originally derived from plasmid pBR322/hag93 which do not have Hind III-cutting site, the Hind III-cutting site is inferred to be generated by the insertion of synthesized Hind III linker into the plasmid in ③-C.

(b) Location of Hind III restriction site on the plasmid

Plasmids of 3 strains of the 4 strains from the group A in ④-E-a are named pFD1, pFD2 and pFD3, respectively. The plasmid carried by one strain of the group B is named pHD-1. The location of Hind III restriction site on each of these 4 plasmids is determined by the rapid plasmid DNA analysis method.

The DNA sample prepared from the strain having each of pFD1, pFD2 and pFD3 by the rapid plasmid DNA analysis method is digested with EcoRI and Hind III and the size of the digested fragments is measured by agarose gel electrophoresis.

Figure 10:
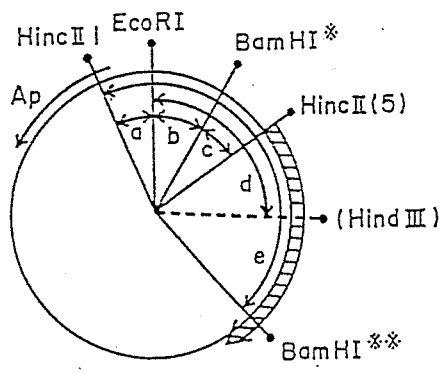
FIG. 10 shows a brief restriction map of pFD1, pFD2 and pFD3.

Fragments of about 5.3 kbp and about 2.3 kbp are observed in all the samples. Accordingly, it is concluded that Hind III restriction site lies at the position about 2.3 kbp apart from EcoRI restriction site ((①-F-b). While the pBR322/hag93 DNA was digested with BamHI into fragments of about 5.8 kbp and about 1.9 kbp ((①-C), the BamHI fragment of 1.9 kbp of pFD1, pFD2 and pFD3 is cut into 2 fragments by digestion with Hind III. This means that the Hind III restriction site of each sample is about 2.3 kbp apart from the EcoRI restriction site in the clockwise direction and lies in the BamHI fragment of about 1.9 kbp. The distance from the EcoRI restriction site to the first BamHI restriction site in the clockwise direction is about 0.7 kbp ((①-C). And the Hind II restriction site ((①-F-b) which exists approximately 70 bp upper site of the initiation codon of the hag gene is about 0.7 kbp distant*¹ from the first BamHI restriction site in the clockwise direction. Accordingly, it is concluded that the EcoRI restriction site is 1.4 kbp distant from the DNA region of the hag gene in the clockwise direction and that the Hind III restriction site about 2.3 kbp apart from the EcoRI restriction site in the clockwise direction lies in the DNA region of the hag gene (see FIG. 10).

*¹ In ①-F-b and FIG. 6 the distance from Hinc II (1) to Hinc II (5) is 1.85 kbp and the distance from EcoRI to BAMHI* is about 0.73 kbp. Besides, the distance from Hinc II (1) to EcoRI is about 0.45 kbp (J. G. Sutcliffe, 1979, Cold Spring Harbor Lab. Symposia 43, p. 83). Accordingly, the distance from BamHI* to Hinc II (5) is about 0.7 kbp.

In a way similar to the above method, the location of Hind III restriction site on the plasmid pHD-1 is determined. It is digested with EcoRI and Hind III into the fragments of about 6.4 kbp and about 1.4 kbp. Accordingly, the Hind III site is clarified to be about 1.4 kbp distance from the EcoRI site. Besides, it is digested with BamHI and Hind III into the fragments of about 5.8 kbp, about 1.2 kbp and about 0.7 kbp. This means that on the plasmid pHD-1 the Hind III site is 1.4 kbp distant from the EcoRI site in the clockwise direction and lies at around Hinc II (5) site in FIG. 10, which is also around the initiation codon ATG of the hag gene.

(C) Analysis of DNA lacking region in plasmid pFD1, pFD2 and pFD3

In the step of in vitro preparation of plasmid pFD1, pFD2 and pFD3 the site cut by DNase I is a little digested with Bal31 (③-B). The deficiency of DNA by this digestion is deduced to be generated where the synthesized Hind III DNA linker is inserted. This position of the insertion is about 2.3 kbp distant from the EcoRI site on the plasmid in the clockwise direction and lies in the Hinc II (5)-Nde1*¹ fragment.

*¹ A restriction enzyme Nde1 restricts a base sequence 5'CA'TATG, which lies at 953th nucleotide in FIG. 9 and at about 2.4 kbp and about 1 kbp downstream from the EcoRI site and the Hinc II (5) site, respectively.

DNAs of pFD1, pFD2, pFD3 and pBR322/hag93 obtained by the rapid method are digested with Hinc II and Ndel and the generated fragments are analysed by the agarose gel electrophoresis.

From FIG. 9 it is deduced that the Hinc II fragment having the hag gene is of the length of 1.7 kbp and digested with Ndel into about 1.0 kbp and 0.7 kbp fragments. In the experiment the Hinc II (5)-Ndel fragments from pBR322/hag93, pFD1, pFD2 and pFD3 are 1,020 bp, 930 bp, 990 bp and 990 bp in length, respectively. Accordingly, it is revealed that the Hinc II (5)-Ndel fragments, which have Hind III site, of pFD1, pFD2 and pFD3 are about 90 bp, about 30 bp and about 30 bp shorter than that of pBR322/hag93, respectively.

(d) DNA sequencing at around Hind III restriction site on pFD1, pFD2 and pFD3.

Figure 11:
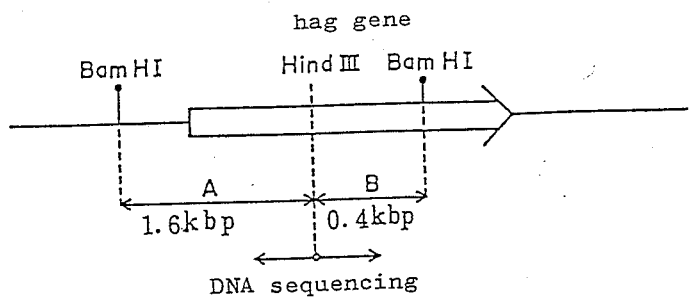
FIG. 11 shows DNA sequencing schedule at around Hind$_{III}$ restriction site on pFD1, pFD2 and pFD4.

The plasmids pFD1, pFD2 and pFD3 are purified by using a host C600r⁻m⁻ hag::Tn10 in the way similar to ①-D-a. DNA sequencing of the purified plasmids at around Hind III site (FIG. 11) is performed by the usual dideoxynucleotide chain termination method using M13 phage. M13mp18 (Pharmacia) is digested with Hind III and BamHI, applied to phenol chloroform extraction and then to ethanol precipitation and dissolved in TE buffer solution. The digested DNA is ligated with T4DNA ligase and introduced into strain JM105 (Pharmacia) to form plaques. According to the usual method, the recombinant M13mp18 DNA having fragment A or B in FIG. 11 is prepared. After cloning on M13mp18 vector as noted above a single strand DNA is prepared and sequenced by the dideoxynucleotide chain termination method.

The hag gene carried on pFD1 lacks 754th to 854th base sequence in FIG. 9, into which the synthesized Hind III linker 5'CAAGCTTG is inserted. As a result an amino acid sequence NDGTVTMAT-GATANATUTDANTTKATTITSGGTP (34 amino acid residues) is lacked and QAC is inserted. The hag gene carried on pFD2 lacks 719th to 765th base sequence in FIG. 9, into which the synthesized Hind III linker 5'CAAGCTTG is inserted. As a result an amino acid sequence DNDGKYYAVTVANDGT (16 amino acid residues) is lacked and ASL is inserted. The hag gene carried on pFD3 lacks 778th to 836th base sequence in FIG. 9, into which the synthesized Hind III linker 5'CAAGCTTG is inserted. As a result an amino acid sequence TGATANATVTDANTTKATTI (20 amino acid residues) is lacked and QAC is inserted.

(e) DNA sequencing at around Hind III restriction site on plasmid pHD1.

Figure 12:
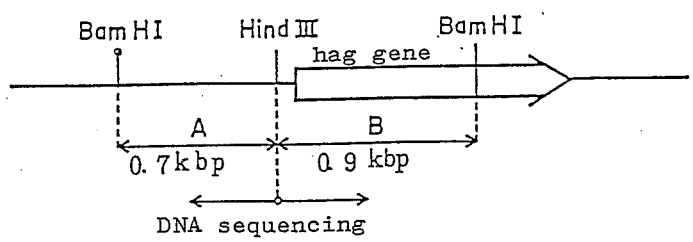
FIG. 12 shows DNA sequencing schedule at around Hind$_{III}$ restriction site on pHD1.

The cc-DNA of pHD1 is purified from the strain C600 r−m− hag::Tn10(pHD1) in the way similar to ①-D-a. The DNA sequencing of the purified plasmid DNA at around Hind III (FIG. 12) is performed by the dideoxynucleotide chain termination method using M13mp18 phage vector as noted in ③-E-d by preparing a single strand DNA of the recombinant M13mp18 having fragment A or B in FIG. 12. As a result, the hag gene carried on pHD1 lacks 8 bases 5'AACGACTT of -28th to -21th in FIG. 9, into which 8 base 5'CAAGCTTG (synthesized Hind III linker) are inserted. This mutation is named pHD1 mutation. It is revealed from the DNA sequencing that the pHD1 mutation did not occur in the region encoding protein in the hag gene. Accordingly, the flagellin coded in the plasmid pHD1 is the same as natural flagellin and so the H antigencity of the constructed flagella also does not alter.

④ The number of flagella of the host strain C600r−m− hag::Tn10 having the plasmid pHD1.

Flagella of C600r−m−hag::Tn10 having each of the pHD1 and pBR322/hag93, which is incubated overnight at 30° C., are dyed. The number of the bacteria having the each number of flagella is counted under an optical microscope (Table 2).

TABLE 2

| The number of bacteria having the each number of flagella | | |
|---|---|---|
| Plasmid Number of flagella | pBR322/hag93 | pHD1 |
| 0 | 249 | 109 |
| 1 | 37 | 79 |
| 2 | 10 | 46 |
| 3 | 2 | 38 |
| 4 | 1 | 15 |
| 5 | 1 | 9 |
| 6 | 0 | 2 |
| 7 | 0 | 1 |
| 8 | 0 | 1 |

The strain C600r−m−hag::Tn10 having the plasmid pHD1 forms the more number of flagella. When the motility is compared between the both strains on the medium for the motility test in the manner similar to ①-A-a, the averages of diameters of motile zones after incubation at 37° C. for 5 hr are 16 mm in pBR322/hag93 and 36 mm in pHD1, which reveals the strain carrying pHD1 has better motility. The hag gene having pHD1 mutation on a multiple copy plasmid such as pBR322 makes host E. coli form a larger number of flagella than that having a natural hag gene on pBR322.

⑤ Construction Of pFD202

(A) Digestion of pFD2 with nuclease Bal31

A cc-DNA of pFD2 is purified from the strain C600r−m−hag::Tn10 (pFD2) in a similar way to ①-D-a. To a mixture of 20 μg/6.2 μl of pFD2 ccDNA, 10 μl of 10×Pvu II buffer solution (100 mM Tris-HCl (pH7.5), 70 mM magnesium chloride, 600 mM sodium chloride and 70 mM 2-mercaptoethanol) and 73.8 μl of water is added 120 units/10 μl of Hind III and allowed to react at 37° C. for 1 hr. The resultant is applied to phenol chloroform extraction and the ethanol precipitation and dissolved in 20 μl of 0.05% bovine serum albumin solution. To 4 μl of the resulting DNA solution is added 4 μl of 2×Bal31 buffer solution (③-B) and incubated at 30° C. for 3 min. Then, 8 μl of nuclease Bal31 (4,900 units/ml) diluted 520 times with Bal31 buffer solution is added thereto and allowed to react at surrounding temperature for 10 min, followed by adding 2 μl of 200 mM EGTA (③-B) thereto and ice-chilling. After phenol chloroform extraction and ethanol precipitation precipitate is dissolved in 10 μl of TE buffer solution.

(B) Repair with klenow fragment and ligation in the presence of synthesized DNA linker (Hind III-Sma I-Bgl II)

To 5 μl of the sample DNA (about 4 μl/10 μl TE buffer solution) in ⑤-A is added 1 μl of 10×nick translation buffer, 4 μl of dNTP's (③-C) and 3 units/1 μl of klenow fragment and allowed to react at room temperature for 30 min. Then, the above reaction mixture is mixed with 5×ligation buffer (③-C), 0.5 μg/1 μl of synthesized DNA linker (Hind III-Sma I-Bgl II, double strands 18 mer polynucleotide 5'AAGCTTCCCG-GGAGATCT3' and 3'TTCGAAGGGCCCT-CTAGA5'; chemically synthesized according to the solid phase synthesis employing triphosphate), 2 μl of 10 mM ATP, 2 μl of 100 mM DTT and 2 μl of water. To the resulting mixture is added 2 units/2 μl of T4DNA ligase and allowed to react at 14° C. for 18 hr.

(C) Selection of transformants

E. coli K-12 C600r−m−hag::Tn10 is transformed with the reaction mixture in ⑤-B. About 1,200 colonies are formed on LB agar medium containing 50 μg/ml ampicillin. These colonies of transformants are inoculated with a sterilized toothpick into the medium for the motility test containing 50 μg/ml ampicillin and incubated at 37° C. for 5-6 hr, about 50% of which show motility. On 90 strains thereof it is investigated whether plasmids carried by them are digested with Sma I using the rapid plasmid DNA analysis method. As a result, plasmids carried by 2 strains are digested with Sma I. A plasmid carried by 1 strain thereof is named pFD202, which is confirmed to be digested also with Hind III and Bgl II by the rapid plasmid DNA analysis method.

(D) DNA sequencing of pFD202 at around the insertion region of synthesized linker The pFD2 is a little digested with nuclease Bal31 from the unique Hind III restriction site to be the plasmid pFD202. Accordingly, the site of the synthesized DNA linker insertion lies at around Hind III site of pFD2 and is included in the about 900 bp fragment generated by digestion of pFD202 with Hinc II and Pst I.

(a) Digestion of pFD202 with Hinc II and Pst I

A cc-DNA of pFD202 is purified from the strain C600r⁻m⁻hag::Tn10 (pFD202) in a manner similar to ①-D-a. The pFD202 cc-DNA (23 μg/10 μl) is mixed with 10 μl of 10×Pvu II buffer solution, 10 μl of 70 mM 2-mercaptoethanol, 5 μl of 0.2% bovine serum albumin, 60 units/10 μl of Hinc II and 96 units/6 μl of Pst I. After the volume is adjusted to 100 μl, the mixture is allowed to react at 37° C. for 80 min. After the reaction 10 μl of 5×sample buffer (25% sucrose, 5 mM sodium acetate, 0.1% sodium dodecyl sulfate and 0.05% brome phenol blue) is added thereto. Its whole volume is applied to electrophoresis of 0.8% agarose gel at 100 V for 40 min. After staining with 0.5 μg/ml ethidium bromide, the gel piece containing the about 900 bp band is cut off. After twice electric extraction at 10 V for 10 min, the resultant is applied to ethanol precipitation and dissolved in 200 μl of TE buffer solution.

(b) Digestion of M13mp8 DNA with Hinc II and Pst I

To a reaction mixture containing 3 μg/30 μl of M13mp8 RFDNA, 10 μl of 10×Pvu II buffer solution, 5 μl of 70 mM 2-mercaptoethanol and 40 μl of water are added 18 units/3 μl of Hinc II and 32 units/2 μl of Pst I and allowed to react at 37° C. for 1 hr. After phenol chloroform extraction and ethanol precipitation, the precipitate is dissolved in 21 μl of TE buffer solution.

(c) Cloning of Hinc II-Pst I fragment in vector M13mp8 and its DNA sequencing

To 21 μl of reaction mixture containing 10 μl of TE buffer solution containing Hinc II-Pst I fragment of ⑤-D-a, 3 μl (about 430 ng DNA) of the sample of ⑤-D-b, 4 μl of 5×ligation buffer, 2 μl of 100 mM DTT and 2 μl of 10 mM ATP is added 1 unit/1 μl of T4DNA ligase and allowed to react at 14° C. for 18 hr. A strain JM109 (Takara Shuzo Co., Ltd.) is transformed with the whole volume of the resulting mixture.

After cloning in a vector M13mp8, the single strand DNA is prepared and sequenced in accordance with the dideoxynucleotide chain termination method. As a result, the hag gene carried on the plasmid pFD202 lacks 78 base pairs (711th to 788th in FIG. 9) from the wild hag gene, where 18 base pairs are inserted. Namely, natural 26 amino acid residues are lacked and artificial 6 amino acid residues are inserted therein in terms of peptide.

⑥ Construction of plasmids pFD301, pFD303, pFD306 and pFD307

(A) Digestion of pFD3 with nuclease Bal31

A cc-DNA of pFD3 is purified from the strain C600r⁻m⁻hag::Tn10 (pFD3) in a way similar to ①-D-a. To a mixture of 50 μg/12 μl of pFD3 ccDNA, 25 μl of 10×Pvu II buffer solution and 188 μl of water is added 300 units/25 μl of Hind III and allowed to react at 37° C. for 1 hr. After the reaction mixture is applied to phenol chloroform extraction and ethanol precipitation in a manner similar to ①-E and the precipitate is dissolved in 25 μl of water. To 5 μl (about 2 μg DNA/μl) of the resulting mixture is added 12.5 μl of 0.2% bovine serum albumin solution and 32.5 μl of water to bring a final DNA conc. of about 200 ng/μl in 0.05% bovine serum albumin. To 20 μl of the solution is added 20 μl of 2×Bal31 buffer solution and incubated at 30° C. for 30 min. A solution (40 μl) prepared by diluting nuclease Bal31 (1,700 units/ml) 1,140 times with Bal31 diluter is added thereto. After reaction at the room temperature for 20 min, 5 μl of 100 mM EGTA is added to 20 μl of the resulting mixture and ice-chilled. After phenol chloroform extraction and ethanol precipitation, the precipitate is dissolved in 10 μl of water.

(B) Repair with klenow fragment and ligation in the presence of synthesized DNA linker (Hind III-Sma I-Bal II)

To the DNA sample (about 1 μg/10 μl) of ⑥-A are added 1.5 μl of 10×nick translation buffer, 2 μl of dNTPs and 3 units/1 μl of klenow fragment and allowed to react at the room temperature for 30 min. Then, to the resulting mixture are added 3.7 μg/5 μl of synthesized DNA linker (Hind III-Sma I-Bgl II), 7 μl of 100 mM DTT, 3 μl of 10 mM ATP, 1 μl of 500 mM Tris-HCl (pH 7.3) and 1.5 μl of water and then added 2 units/2 μl of T4DNA ligase and allowed to react at 15° C. for 18 hr.

(C) Selection of transformants

After dialyzing the resulting mixture of ⑥-B against TE buffer solution for about 4 hr, E. coli K-12 C600r⁻m⁻hag::Tn10 is transformed with the resultant. About 560 colonies of transformants are formed on LB agar medium containing 50 μg/ml of ampicillin. These colonies are inoculated with a sterilized toothpick into the medium for the motility test containing 50 μg/ml of ampicillin. Including strains showing weak motility, 23 motile strains are picked up. It is investigated on these 23 strains whether plasmids carried by them are digested with Sma I and as a result 4 strains are selected. Plasmids carried by the 4 strains are named pFD301, pFD303, pFD306 and pFD307. These 4 plasmids are confirmed to be digested with Hind III and Bgl II by the rapid plasmid DNA analysis.

(D) DNA sequencing of pFD301, pFD303, pFD306 and pFD307 at around an insertion region of synthesized DNA linker.

Figure 13:
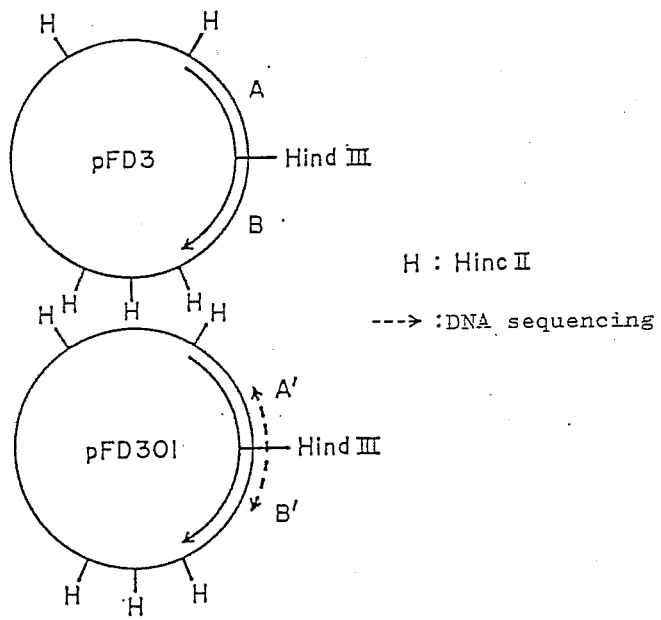
FIG. 13 shows pFD3 and pFD301.

The plasmids pFD301, pFD303, pFD306 and pFD307 derives from FD3 by the digestion with nuclease Bal31 from Hind III restriction site. Therefore, an insertion region of synthesized DNA linker on pFD301, pFD303, pFD306 and pFD307 lies at around Hind III restriction site of pFD3. Accordingly, DNA sequencing at around the insertion region of synthesized DNA linker is achieved from Hind III site of 2 Hind III-Hinc II fragments A' and B' (see FIG. 13):

(a) Digestion of pFD301, pFD303, pFD306 and pFE307 with Hinc II and Hind III

A cc-DNA is purified from C600r⁻m⁻hag::Tn10 having each of pFD301, pFD303, pFD306 amd pFD307 according to ①-D-a. To a mixture of 5 μg of pFD301 ccDNA, 5 μl of 10×Pvu II buffer solution, 5 μl of 70 mM 2-mercaptoethanol, 30 units/5 μl of Hinc II and 50 units/5 μl of Hind III is added water for adjusting the volume to 50 μl and incubated at 37° C. for 1 hr. After phenol chloroform extraction and ethanol precipitation, the precipitate is dissolved in 10 μl of water. The same treatment is performed on pFD303, pFD306 and pFD307.

(b) Digestion of M13mp18 RFDNA with Hinc II and Hind III

To a reaction mixture containing 2.5 μg/5 μl of M13mp18 RFDNA, 5 μl of 10×Pvu II buffer solution, 5 μl of 70 mM 2-mercaptoethanol and 25 μl of water are added 30 units/5 μl of Hinc II and 50 units/5 μl of Hind III and allowed to react at 37° C. for 1 hr. After phenol chloroform extraction and ethanol precipitation, the precipitate is dissolved in 10 μl of water.

(c) Cloning of Hinc II-Hind III fragment in vector M13mp18 and its DNA sequencing To a mixture containing 1.5 μg/3 μl of Hinc II-Hind III fragment in ⑥-D-a, 0.5 μg/2 μl of the sample in ⑥-D-b, 4 μl of 5×ligation buffer. 2 μl of 100 mM DTT, 2 μl of 10 mM ATP and 5 μl of water is added 2 units/2 μl of T4DNA ligase and incubated at 15° C. for 18 hr. The strain JM109 (Takara Shuzo Co., Ltd.) is transformed with the whole volume of the resulting mixture. Picking up 10 plaques, a single strand DNA is prepared in accordance with the usual method. A double strand DNA digested with Hinc II and Hind III is investigated by 1.6% agarose gel electrophoresis (pFD3 cc-DNA digested with Hinc II and Hind III is used as a control of size of DNA fragment). As a result both of the fragments A and B derived from pFD3 ccDNA are disappeared but in place of them fragments A' and B' shorter than fragments A and B are observed. Each sample of the single strand DNA having the above both fragments is applied to DNA sequencing according to the dideoxynucleotide chain termination method. As a result the hag gene carried on pFD301 lacks 561 base pairs (583th to 1,143th), compared with the wild hag gene, into which 18 base pairs are inserted. Namely, natural 187 amino acid residues are lacked from the wild type flagella and artificial 6 amino acid residues are inserted to the pFD301-coded flagellin (FIG. 14-A). The sequences of hag genes of pFD303, pFD306 and pFD307 are shown in FIGS. 14-B, C, and D, respectively.

⑦ Construction of pFD311, pFD313 and pFD315

The plasmids pFD311, pFD313 and pFD315 are constructed in the same way as ⑥-A, ⑥-B, ⑥-C and ⑥-D except that the time of the reaction of nuclease Bal31 is 5 min. The DNA sequences of the plasmids pFD311, pFD313 and pFD315 are shown in FIGS. 15-A, B and C, respectively.

⑧ Excretion of Flagellin Fused with Polypeptide HBsAG-I by Plasmid Vector pFD1

(A) Digestion of pFD1 with Hind III and repair with klenow fragment

To a mixture containing 20 μg of pFD1 cc-DNA, 10 mM Tris-HCl (pH7.5), 7 mM magnesium chloride and 60 mM sodium chloride is added 100 units of Hind III and allowed to react at 37° C. for 30 min. After phenol chloroform extraction and ethanol precipitation, the precipitate is dissolved in 20 μl of TE buffer solution.

To the above DNA (20 μg/20 μl TE buffer solution) are added 2 μl of 10×nick translation buffer, 2 μl of dNTP (1 mM of each XTP) and 3 units/1 μl of klenow fragment and allowed to react at room temperature for 30 min. Then, 1 μl of 500 mM EDTA is added thereto. After phenol chloroform extraction and ethanol precipitation, the precipitate is dissolved in 20 μl of TE buffer solution.

(B) Annealing of synthesized polynucleotide

To synthesized polynucleotide RTH-1603 (5'A-CAAAACCTACGGATGGAAATGG3', about 20 μg/100 μl of water) and synthesized RTH-1604 (5'CCATTTCCATCCGTAGGTTTTGT3', abount 20 μg/100 μl water) is added 20 μl of 10×TE buffer solution. Annealing is achieved by allowing it to stand at 60° C. for 30 min and gradually cooling to 28.5° C. in 6 hr.

(C) Ligation of synthesized DNA with pFD1

A mixture containing 1 μg/1 μl of the DNA of ⑧A, 180 pmol/13 μl of the synthesized DNA of ⑧B, 4 μl of 5×ligation buffer and 5.6 units/2 μl of T4DNA ligase is allowed to react at 16° C. for 16 hr and the resulting mixture is dialyzed against TE buffer solution for 2 hr.

(D) Selection of transformants

A strain C600r⁻m⁻hag::Tn10 is transformed with the DNA of ⑧-C. On LB medium containing 50 μg/ml ampicillin are formed 3.8×10⁴ ampicillin-resistant colonies per 1 μg of pFD1 DNA. Motility of 90 colonies thereof is investigated and 82 strains show motility. The rapid plasmid analysis is achieved on 62 strains thereof and as a result 5 strains #11, #12, #14, #16 and #17 have a plasmid that is not digested with Hind III. The plasmids carried by these 5 strains are named pFD1/HBsAG-I #11, #12, #14, #16 and #17.

(E) DNA sequencing at around synthesized DNA inserted into pFD1/HBSAg-I

A region into which the synthesized DNA fragment is inserted on pFD1/HBsAg-I is included in the 3rd largest fragment among fragments generated by digestion with Hinc II and Pst I.

(a) Digestion of pFD1/HBsAg-I with Hinc II and Pst I

Each of the 5 strains #11, #12, #14, #16 and #17 of ⑧-D is incubated in 10 ml of LB broth containing 50 μg/ml of ampicillin. A sample of each strain for the rapid plasmid DNA analysis is prepared and dissolved in 150 μl of TE buffer solution.

To the above sample are added 22 μl of 10×Pvu II buffer solution, 22 μl of 70 mM 2-mercapto-ethanol, 11 μl of 0.2% bovine serum albumin, 80 units/10 μl of Hinc II and 90 units/12 μl of Pst I and allowed to react at 37° C. for 1 hr.

The resulting mixture is concentrated to 100 μl with a centrifuge evaporator to which 10 μl of sample buffer is added. The resultant is subjected to 0.8% agarose gel electrophoresis and the gel piece including the 3rd largest fluorescent band is cut off and applied to electric extraction and ethanol precipitation. The precipitate is dissolved in 15 μl of TE buffer solution.

(b) Digestion of M13mp18 RFDNA with Hinc II and Pst I

M13mp18 RFDNA is digested with Hinc II and Pst I according to ⑤-D-b except that 2 μg/4 μl of M13mp18 RFDNA in place of M13mp8 RFDNA and 66 μl of water are used.

(c) Cloning of Hinc II-Pst I fragment in M13mp18 and DNA sequencing

To 4 μl of each DNA sample of strains #11, #12, #14, #16 and #17 of ⑧-E-a is added 4 μl (400 ng) of DNA sample of ⑧-E-b and then added 4 μl of 5×ligation buffer, 2 μl of 100 mM DTT, 2 μl of 10 mM ATP, 1 μl of water and 1 unit/1 μl of T4DNA ligase and allowed to react at 16° C. for 16 hr. A strain JM109 is transformed with the whole volume of the resultant. After cloning in vector M13mp18, a single strand DNA is prepared and applied to the dideoxynucleotide chain termination method for DNA sequencing. As a result a sequence at around synthesized DNA in each plasmid is clarified as follows.

pFD1/HBsAG I #11
AlaGluAlaThrLysProThrAspGlyAsnGlyAlaCys-Val
5'GCTCAAGCTACAAAACCTACGGATG-GAAATGGAGCTTGTGTT pFD1/HBsAG-I #12, #14, #16, ·17
AlaGlnAlaProPheProSerValGlyPheValAlaCysVal
5'GCTCAAGCTCCATTTCCATCC-GTAGGTTTTCTAGCTTGTGTT

Underlined is a synthesized DNA inserted.

⑨ Excretion of Flagellin Fused with Polypeptide HBsAg-II by Plasmid Vector pFD1

(A) Digestion of pFD1 cc-DNA with Hind III and repair with klenow fragment

A pFD1 cc-DNA is digested with Hind III and repaired with klenow fragment according to ⑧-A (B) Annealing of synthesized polynucleotide Synthesized RSM-2103 (5'ACAAACCTTC-GGATGGAAATGG3') and RSM-2104 (5'CCATTT-CCATCCGAAGGTTTTGT3') are annealed in a way similar to ⑧-B.

(C) Ligation of synthesized DNA with vector pFD1.

The synthesized DNA is ligated with vector pFD1 in accordance with ⑧-C.

(D) Selection of transformants

A strain C600r⁻m⁻hag::Tn10 is transformed with the sample DNA in ⑨-C. On LB medium containing 50 μg/ml of ampicillin 2×10⁴ ampicillin-resistant colonies per 1 μg of pFD1 DNA are formed. Motility of 68 colonies thereof is investigated and 43 strains thereof show motility. Plasmids carried by 16 strains thereof are applied to the rapid plasmid analysis in accordance with ⑧-D. As a result it is revealed that plasmids carried by 7 strains #1, #2, #3, #6, #8, #13 and #16 are not digested with Hind III. The plasmids carried by them are named pFD1/HBsAG-II #1, #2, #3, #6, #8, #13 and #16.

(E) Sequencing at around synthesized DNA inserted into pFD1/HBsAg-II

DNA sequencing is achieved on pFD1/HBsAg-II #1 and pFD1/ HBsAg-II #13 according to ⑧-E. The sequence at around the synthesized DNA on bots plasmids is shown below. pFD1/HBsAG II #1, pFD1/HBsAg II #13, pFD1/HBsAg-II #1, pFD1/HBsAG II #13
AlaGluAlaThrLysProSerAspGlyAsnGlyAlaCysVal
5'GCTCAAGCTACAAAACCTTCGGATG-GAAATGGAGCTTGTGTT Underlined is a synthesized DNA.

⑩ Increase of the Number of Flagella by pHD1 Mutation (A) Prepartion of cc-DNAs of plasmids pFD1, pFD1/HBsAg-I and pFD1/HBsAg-II from dam⁻ strain A DNA sample for the rapid plasmid analysis is prepared from a strain having each of pFD1, pHD1, pFD1/HBs Ag-I #11, pFD1-HBsAg-II #1 by using a strain C600r⁻m⁻hag::Tn10. A strain GM33 dam⁻ is transformed with each of the above samples to establish GM33dam⁻ (pFD1), GM33dam⁻ (pHD1, GM33dam⁻ (pFD1/HBsAG-I #11) and GM33dam⁻ (pFD1/HBsAg-II #1). A cc-DNA is purified from each strain according to ①-D-a.

(B) Preparation of EcoRI-Bcl I fragment (about 1.4 kbp) from plasmid pHD1

To 29.7 μg/25 μl of pHD1 cc-DNA of ⑩-A are added 20 μl of 10×Bcl I buffer solution (500 mM Tris-HCl (pH 8.0), 100 mM magnesium chloride and 500 mM sodium chloride), 20 μl of 70 mM 2-mercaptoethanol, 10 μl of 0.2% bovine serum albumin, 75 units/10 μl of EcoRI and 105 μl of water and allowed to react at 37° C. for 1 hr. Then, 50 units/5 μl of Bcl I is added thereto and allowed to react at 50° C. for 1 hr. A mixture of 189 μl of the resultant and 20 μl of sample buffer is applied to 0.8% agarose gel electrophoresis. A fluorescent band corresponding to approximately 1.4 kbp is cut off, applied to electric extraction and dissolved in 30 μl of TE buffer solution.

(C) Digestion with EcoRI, treatment with alkaline phosphatase (BAP) and partial digestion with Bcl I on pFD1, pFD1/HBsAg-I #11 and pFD1/HBssAf-II 1

To 40 μg/40 μl of each pFD1, pFD1/HBsAg-I #11 and pFD1/HBsAg-II #1 are added 16 μl of 10×EcoRI buffer solution (1M tris-HCL (pH 7.5), 70 mM magnesium chloride and 500 mM sodium chloride), 16 μl of 70 mM 2-mercaptoethanol, 8 μl of 0.2% bovine serum albumin and 60 units/8 μl of EcoRI and allowed to react at 37° C. for 30 min. After adjusting the volume to 160 μl by adding water, the resultant is allowed to react at 37° C. for 1 hr. Then, to each sample are added 6 μl of 1M Tris-HCl (pH8.0), 1.2 units/10 μl of BAP and 25 μl of water and allowed to react at 65° C. for 30 min.

After phenol chloroform extraction and ethanol precipitation, the precipitate is dissolved in 100 μl of TE buffer solution. To 8 μg DNA/20 μl of the each sample are added 8 μl of 10×Bcl I buffer solution, 4 μl of 0.2% bovine serum albumin, 44 μl of water and 2 units/4 μl of Bcl I and allowed to react at 50° C. for 40 min. After phenol chloroform extraction and ethanol precipitation, the precipitate is dissolved in 40 μl of TE buffer solution.

(D) Ligation

To a mixture containing about 90 ng/30 μl of the DNA sample of ⑩-B, 800 ng/4 μl of the DNA sample of ⑩-C, 3 μl of 10×ligation buffer, 3 μl of 100 mM DTT, 3 μl of 10 mM ATP and 12 μl of water is added 2 units/2 μl of T4DNA ligase and allowed to react at 16° C. for 16 hr.

(E) Trasformation

The DNA sample of ⑩-D is dialyzed against TE buffer solution for 3 hr, with which a strain C600r⁻m⁻hag::Tn10 is transformed. On LB medium containing 50 μg/ml of ampicillin are formed 2.6×10⁵ colonies per 1 μg of the treated pFD1 DNA, 3.75×10⁵ colonies per 1 μg of treated pFD1/HBsAg-I #11 DNA and 2.4×10⁵ colonies per 1 μg of treated pFD1/HBsAg-II #1 DNA.

(F) Motility of transformants and HindIII site on plasmids carried thereby

Motility of the transformants of ⑩-E is investigated. Eleven strains of 45 transformants by the treated pFD1 show motility. With regard to treated pFD1/HBsAg-I #11 and treated pFD1/HBsAg-II #1, 12 strains of 45 transformants by each plasmid shown motility. DNA samples of these 11 strains, 12 strains and 12 strains for the rapid plasmid DNA analysis are prepared. A mixture containing 7 μl of the DNA sample for the rapid plasmid DNA analysis, 1 μl of 10×EcoRI buffer solution, 1 μl of 70 mM 2-mercaptoethanol, 0.5 μl of 0.2% bovine serum albumin, 4 units/0.5 μl of EcoRI and 5 units/0.5 μl of HindIII is allowed to react at 37° C. for 30 min. DNA fragments generated by 0.8% agarose gel electrophoresis are investigated. A plasmid which generated 3 fragments containing 1.4 kbp and 0.7 kbp fragments is found from the 11 strains having the treated pFD1 and named pHFD1. The strain having this plasmid is purified to establish a strain C600r⁻m⁻hag::Tn10(pHFD1). A plasmid which generated 2 fragments containing 1.4 kbp fragment is found from the 12 strains having the treated pFD1/HBsAg-I #11 and named pHFD1/HBsAg-I #11. The strain having this plasmid is purified to establish a strain C600⁻m⁻hag::Tn10 (pHFD1/HBsAg-I #11). Similarly, a plasmid which generated 2 fragments containing 1.4 kbp fragment is found from the 12 strains having the treated pFD1/HBsAg-II #1 and named pHFD1/HBsAg-II #1. The strain having the plasmid is purified to establish a strain C600r⁻m⁻hag::Tn10 (pHFD1/HBsAg-II #1).

(G) Motility depending on plasmid which carries hag gene having pHD1 mutation

Motility of 5 strains C600r⁻m⁻(pBR322), C600r⁻m⁻hag::Tn10 (pFD3), C600r⁻m⁻hag::Tn10 (pHFD1), C600r⁻m⁻hag::Tn10 (pHFD1/HBsAg-I #11) and C600r⁻m⁻hag::Tn10 (pHFD1/HBsAg-II #1) is investigated. The 5 strains are purified in LB broth containing 50 μg/ml of ampicillin. After incubating overnight at 37° C., colonies are inoculated into the medium for the motility test (1% Bactotryptone, 0.25% sodium chloride, 5 μg/ml of thiamine and 0.3% agar, pH7.0). After incubating at 37° C. or 30° C. for 6 hr, the diameter of the motile zone is measured (Table 3).

TABLE 3

| Strain | Diameter of motile zone (mm) | |
|---|---|---|
| | 37° C. | 30° C. |
| C600rm(pBR322) | 43 | 34 |
| C600rmhag::Tn10(pFD3) | 34 | 20 |
| C600rmhag::Tn10(pHFD1) | 41 | 34 |
| C600rmhag::Tn10(pHFD1/HBsAg I #11) | 38 | 32 |
| C600rmhag::Tn10(pHFD1/HBsAg II #1) | 43 | 31 |

The strain C600r⁻m⁻hag::Tn10 having pHFD1, pHFD1/HBsAg-I #11) or pHFD1/HBsAg-II #1 presents motility better than the strain having pFD3 and similar to that of the natural strain C600r⁻m⁻(pBR322).

⑪ Excretion of Flagellin Fused with Polypeptide HBsAg-II by pFD1, pFD303, pFD306, pFD307, pFD311 and pFD315

(A) Digestion of cc-pFD1, cc-pFD303, cc-pFD306, cc-pFD307, cc-pFD311 and cc-pFD315 with HindIII and repair with klenow fragment According to ⑧-A, cc-pFD1, cc-PFD303, cc-pFD306, cc-pFD307, cc-pFd311 and cc-pFD315 each is digested with HindIII and repaired with klenow fragment.

(B) Construction of synthesized polynucleotide

Synthesized polynucleotides HBsAgA-1*[1], HBsAgA-2*[2], HBsAgA-3*[3], HBsAgA-4*[4] and HBsAgA-5*[5] as noted below are synthesized according to the solid phase phosphoroamidite method using ZEON GENET A-II (Zeon).

*[1] 5'TTGACACGTATCCTCACAATACCGCAGTC 3'  *[2] 5'ACTAGACTCGTGGGG 3'  *[3] 5'GAGGATACGTGTCAA 3'  *[4] 5'CTAGTGACTGCGGTATTGT 3'  *[5] 5'CCCCACGAGT 3'

To HBsAgA-2 (500pM/12.2 μl), HBsAgA-3 (500pM/12.2 μl) and HBsAgA-4 (500pM/15.4 μl) each of which is in a 1.5 ml-eppendolf tube are added 19.8 μl, 19.8 μl and 16.6 μl of water, respectively. To each tube are added 10 μl of 10×kinase buffer solution I (0.5M Tris-HCl (pH 7.6), 0.1M magnesium chloride, 50 mM dithiothreitol, 1 mM spermidine and 1 mM EDTA), 1 μl of γ-³²P ATP (5,000Ci/mM: 10 μC/μl, Amersham), 5 μl of 10 μM ATP and 2 μl of T4 polynucleotide kinase (Takara Shuzo Co., Ltd.) and allowed to react at 37° C. for 30 min. Further, 2.5 μl of 1 mM ATP and 5 units/2 μl of T4 polynucleotide kinase are added thereto, allowed to react at 37° C. for 1 hr, heated to 90° C. for 5 min and rapidly chilled in ice.

The all of the above reaction mixture of HBsAgA-2, HBsAgA-3 and HBsAgA-4 are mixed with HBsAgA-1 (500pM/23.5 μl) and HBsAgA-5 (500pM/8.1 μl). The mixture is put in a dialyze membrane (spectra pore/molecular weight cut off 1,000, spectrum medical industry) and dialysed overnight at 4° C. against water. The resultant is placed in a 1.5 ml-eppendolf tube and concentrated with a centrifuge evaporator. the concentrated mixture is dissolved in 15 μl of Tris-HCl containing 10 mM magnesium chloride, heated to 60° C. for 30 min and gradually cooled to room temperature in 6 hr. To the resulting mixture are added 16 μl of 5×ligation buffer, 4 μl of 200 mM DTT, 10 mM ATP, 22.4 units/8 μl of T4DNA ligase and 37 μl of water and allowed to react at 15° C. for 16 hr. The resultant is applied to 15% polyacrylamide gel electrophoresis and then to autoradiography. The band corresponding to 44 bp is cut off, placed in a 1.5 ml-eppendolf tube and broken with a glass rod. The resultant is extracted with 1 ml of water at 4° C. for 16 hr. After centrifugation, the supernatant (about 700 μl) is concentrated with a centrifuge evaporator. The concentrate (about 200 μl) is centrifuged again to remove residues of the gel.

(C) Ligation of synthesized DNA with pFD1, pFD303, pFD306, pFD307, pFD311 and pFD315

A mixture containing 500 ng/1 μl of the DNA sample of ⑪-A, 250pM/100 μl of the synthesized DNA of ⑪-B, 4 μl of 5×ligation buffer, 2 μl of 200 mM DTT, 2 μl of 10 mM ATP, 2 μl of T4DNA ligase and 4 μl of water is allowed to react at 15° C. for 16 hr. After dialysing against TE buffer solution, the whole volume of the resultant is used for transformation.

(D) Selection and motility of transformants

A strain C600r⁻m⁻hag::Tn10 is transformed with the DNA sample of ⑪-C. On LB medium containing 50 μg/ml of ampicillin are formed 5×10⁴ colonies/1 μg pFD1DNA, 2×10⁵ colonies/1 μg pFD303DNA, 1.8×10⁵ colonies/1 μg pFD306DNA, 2.3×10⁴ colonies/1 μg pFD307DNA, 1.3×10⁵ colonies/1 μg pFD311DNA and 8×10⁴ colonies/1 μg pFD315DNA.

Motility of 100 strains of each group is investigated on the medium for the motility test. Of colonies showing motility, 6 motile strains of each group are incubated overnight in LB medium containing 50 μg/ml of ampicillin. Then it is investigated whether HindIII restriction site lies on the plasmid carried by the strains. Since HindIII site on the plasmid is cut with HindIII and repaired with klenow fragment, HindIII is generated again where the synthesized DNA HBsAg-III is inserted thereto in a right direction and, as a result, provides T of 5' terminal of the synthesized DNA to the restriction site. Where the synthesized DNA is inserted in a reverse direction or not inserted, HindIII site is not generated. Accordingly, the synthesized DNA is inserted in a right direction if a short fragment is generated when the plasmid is digested with HindIII and SstII (SstII site lies downstream of the insertion site at a short distance), and the synthesized DNA is inserted in a reverse direction or not inserted if a short fragment is not generated. Thus, it can be investigated whether the synthesized DNA is inserted in a right direction. Therefore, a plasmid DNA prepared from each strain by the rapid method is digested with HindIII and SstII. A mixture containing 8 μl of the sample of a plasmid, 2 μl of 10× SstII buffer solution (500 mM Tris-HCl (pH 8.0), 100 mM magnesium chloride and 500 mM sodium chloride), 2 μl of 70 mM 2-mercaptoethanol, 10 units/1 μl of HindIII, 7 units/1 μl of SstII and 6 μl of water is allowed to react for digestion. After 5% polyacrylamide electrophoresis (150 V, 95 min) and ethidium bromide-staining, it is investigated whether a band corresponding to the short fragment is observed. As a result, 2 strains are established from each group. They show motility and have a plasmid into which the synthesized DNA is inserted in a right direction. These strains excrete flagellin fused with peptide LeuThrArgIleLeuThrIleProGlnSerLeuAsp-SerTrpGly encoded by the synthesized DNA (HBsAg-III) inserted in the plasmid. Also, this fused flagellin can construct the flagella.

⑫ Excretion of Flagellin Fused with Polypeptide HBsAg-IV by pFD1, pFD303, pFD306, pFD307, pFD311 and pFD315

(A) Digestion of cc-pFD1, cc-pFD303, cc-pFD306, cc-PFD307, cc-pFD311 and cc-pFD315 with HindIII and repair with klenow fragment According to ⑪ -A, cc-pFD1, cc-pFD303, cc-pFD306, cc-pFD307, cc-pFD311 and cc-pFD315 are digested with HindIII and repaired with klenow fragment.

(B) Contruction of synthesized polynucleotide

Synthesized polynucleotides HBsAgB-1*1, HBsAgB-2*2, HBsAgB-3*3, HBsAgB-4*4, HBsAgB-5*5 and HBsAgB-6*6 as noted below are synthesized according to ⑪ -B.

*1 5′TTGGTTCTTCTGGATTAT 3′ *2 5′CAGAAGAACCAA 3′ *3 5′CAAGGTATGTTGCCCGT 3′ *4 5′AACATACCTT-GATAATC 3′ *5 5′TTGTCCTCTAGG 3′ *6 5′CCTAGAG-GACAAACGGGC 3′

To HBsAgB-2 (50pM/9.7 μl), HBsAgB-5 (500 mM/9.7 μl), HBsAgB-3 (500pM/13.8 μl) and HBsAgB-4 (500pM/13.8 μl) each of which is in a 1.5 ml-eppendolf tube are added 22.3 μl, 22.3 μl, 18.2 μl, and 18.2 μl of water, respectively. According to 11 -B, synthesized polynucleotides are phosphatized at 5′ terminal. The above whole reaction mixtures are mixed with 14.6 μl of HBsAgB-1 and 14.6 μl of HBsAgB-6 and ligated according to 11 -B. Then, the resultant is separated by polyacrylamide gel electrophoresis to give 200 μl of sample DNA.

(C) Ligation of synthesized DNA with pFD1, pFD303, pFD306, pFD307, pFD311 and pFD315

According to 11 -C, HBsAg-IV is ligated with a plasmid and the whole volume of the resultant is used for transformation.

(D) Selection of transformants and their motility

A strain C600r−m−hag::Tn10 is transformed with the sample DNA of 12 -C. On LB media containing 50 μg/ml of ampicillin are formed $4.4\times10^4$ colonies/1 μg pFD1 DNA, $2.9\times10^4$ colonies/1 μg pFD303 DNA, $3.8\times10^4$ colonies/1 μg pFD306 DNA, $3.2\times10^4$ colonies/1 μg pFD307 DNA, $1.4\times10^5$ colonies/1 μg pFD311 DNA and $5.8\times10^4$ colonies/1 μg pFD315 DNA. From each group are selected 6 strains showing motility, which are investigated whether they have a plasmid into which the synethesized DNA HBsAg-IV is inserted in a right direction. Two strains are established from each group. These strains excrete flagellin fused with peptide LeuValLeuLeuAspTyr-GlnGlyMetLeuProValGysProLeuGly encoded by the synthesized DNA (HBsAg-IV) which is inserted in the plasmid and form flagella.

Referential Examination

Transformation of *E. coli* JA11 with pBR322/hag93

*E.coli* JA11 (FERM P-8853) is incubated to be competent according to the method of Hanahan et al. (J. Mol. Biol 166, 557–580, 1983). The competent cells (210 μl) of strain JA11 frozen at −70° C. are melted and 200 ng of pBR322/hag93 cc-DNA dissolved in TE buffer solution in ice at 0° C. is added thereto. After allowed to stand in ice at 0° C. for 30 min and heated to 42° C. for 100 sec, to the mixture is added 0.8 ml of SOC broth. After incubation at 37° C. for 1 hr with shaking, the culture is diluted $10^4$ times, 0.1 ml of which is spread on LB agar medium containing 50 μg/ml of ampicillin. After overnight incubation at 37° C., 52 colonies are formed. This means that the strain JA11 is transformed with pBR322/hag93, at a ratio of $2.6\times10^7$ colonies/1 μg cc-DNA.

What is claimed is:

1. A DNA comprising: a DNA sequence containing the hag gene which encodes flagellin of *Escherichia coli* or a DNA sequence containing said hag gene but lacking an antigenic portion of said hag gene between the base pairs 583 and 1143; and a DNA sequence which encodes a peptide foreign to *Escherichia coli,* wherein said DNA sequence encodes a fused protein which is capable of being excreted through the cell wall of an *Escherichia coli* host.

2. The DNA of claim 1, wherein said *Escherichia coli* is *Escherichia coli* K-12.

3. The DNA of claim 2, wherein said *Escherichia coli* K-12 is *Escherichia coli* K-12HK552.

4. The DNA of claim 1, wherein said DNA sequence is as shown in FIG. 1.

5. The DNA of claim 1, wherein said DNA comprises a region corresponding to the hag gene but lacking said portion of said hag gene which affects the antigenicity of said flagellin.

6. The DNA of claim 5, wherein said DNA sequence which encodes said peptide foreign to *Escherichia coli* is inserted into said hag gene in said section between base bairs 583 and 1143.

7. The DNA of claim 5, wherein the entire portion of said hag gene from the 583rd to 1,143th bases is lacking.

8. The DNA of claim 7, which contains an 18mer linker in said lacking portion.

9. The DNA of claim 1, which comprises a sequence corresponding exactly to FIG. 1.

10. The DNA of claim 1, which comprises the sequence shown in FIG. 14-A.

11. The DNA of claim 1, which comprises the sequence shown in FIG. 15-A.

12. The DNA of claim 1, which comprises the sequence shown in FIG. 15-B.

13. The DNA of claim 1, which comprises the sequence shown in FIG. 15-C.

14. The DNA of claim 1, which codes for flagellin fused with polypeptide HBsAg-II, HBsAg-III on HBsAg-IV.

15. An expression vector capable of expressing a fused protein of flagellin of *Escherichia coli* or a part thereof and a protein foreign to *Escherichia coli* comprising: an expression vector; a DNA sequence coding the hag gene which encodes flagellin of *Escherichia coli* or a DNA sequence containing said hag gene but lacking an antigenic portion of said hag gene between the base pairs 583 and 1143; and a DNA sequence which encodes a peptide foreign to *Escherichia coli*, wherein said DNA sequence encodes a fused protein which is capable of being excreted through the cell wall of an *Escherichia coli* host.

16. The vector of claim 15, which is a plasmid.

17. The vector of claim 15, which is a phage.

18. The vector of claim 15, which is capable of transforming a bacteria which does not form flagella into a bacteria having flagella.

19. The vector of claim 15, wherein said DNA sequence is as shown in FIG. 1.

20. The vector of claim 15, wherein said DNA comprises a region corresponding to the hag gene but lacking a portion of the hag gene which affects the antigenicity of said flagellin.

21. The vector of claim 20, wherein the entire portion of said hag gene from the 583rd to 1,143rd bases is lacking.

22. The vector of claim 15, wherein said DNA sequence for said peptide foreign to *Escherichia coli* is inserted into said antigenic portion.

23. A microorganism containing the expression vector of claim 15, which is capable of excreting said fused protein.

24. The microorganism of claim 23, wherein said fused protein forms flagella which provide motility to said microorganism.

25. The microorganism of claim 24, which is *Escherichia coli.*

26. A microorganism containing the expression vector of claim 19, which is capable of excreting said fused protein.

27. A microorganism containing the expression vector of claim 20, which is capable of excreting said fused protein.

28. A microorganism containing the expression vector of claim 21, which is capable of excreting said fused protein.

29. A microorganism containing the expression vector of claim 22, which is capable of excreting said fused protein.

30. *E. coli* K-12 JA11 (FERM BP-1233).

31. *E. coli* K-12 W3623Hfla-am 76 (FERM BP-1231).

* * * * *